US011795120B2

(12) United States Patent
Timmusk

(10) Patent No.: US 11,795,120 B2
(45) Date of Patent: Oct. 24, 2023

(54) RHIZOBACTERIA AND USES THEREOF

(71) Applicant: Salme Timmusk, Uppsala (SE)

(72) Inventor: Salme Timmusk, Uppsala (SE)

( * ) Notice: Subject to any disclaimer, the term of this patent is extended or adjusted under 35 U.S.C. 154(b) by 668 days.

(21) Appl. No.: 16/841,036

(22) Filed: Apr. 6, 2020

(65) Prior Publication Data

US 2020/0260736 A1 Aug. 20, 2020

Related U.S. Application Data

(63) Continuation of application No. 14/423,175, filed as application No. PCT/SE2013/050998 on Aug. 26, 2013, now abandoned.

(30) Foreign Application Priority Data

Aug. 27, 2012 (SE) .................................... 1250955-0

(51) Int. Cl.
*C05F 11/00* (2006.01)
*C12N 1/20* (2006.01)
*A01N 63/25* (2020.01)
*C05F 11/08* (2006.01)

(52) U.S. Cl.
CPC .............. *C05F 11/00* (2013.01); *A01N 63/25* (2020.01); *C05F 11/08* (2013.01); *C12N 1/20* (2013.01)

(58) Field of Classification Search
None
See application file for complete search history.

(56) References Cited

U.S. PATENT DOCUMENTS

| | | | | |
|---|---|---|---|---|
| 5,683,691 | A | 11/1997 | Peferoen et al. | |
| 2003/0228679 | A1 | 12/2003 | Smith et al. | |
| 2007/0248583 | A1* | 10/2007 | Kochi .................... | A01N 63/25 424/93.46 |

FOREIGN PATENT DOCUMENTS

| | | | |
|---|---|---|---|
| WO | 99/09834 | A2 | 3/1999 |
| WO | 2009/091557 | A1 | 7/2009 |

OTHER PUBLICATIONS

Lucian Copolovici et al., Flooding induced emissions of volatile signalling compounds in three tree species with differing waterlogging tolerance, Plant, Cell & Environment, 33:1582-1594 (2010).
A. Marulanda et al., An Indigenous Drought-Tolerant Strain of Glomus intraradices Associated with a Native Bacterium Improves Water Transport and Root Development in Retama sphaerocarpa, Microbial Ecology, vol. 52:670-678 (online Oct. 31, 2006).
Satish V. Patil et al., Bioflocculant Exopolysaccharide Production by Azotobacter indicus Using Flower Extract of *Madhuca latifolia* L, Appl Biochem Biotechnol, 162:1095-1108 (2010).
Marcello Iriti et al., Chemical Diversity and Defence Metabolism: How Plants Cope with Pathogens and Ozone Pollution, Int. J. Mol. Sci., 10:3371-3399 (Jul. 30, 2009).
Salme Timmusk et al., Bacterial Distribution in the Rhizosphere of Wild Barley under Contrasting Microclimates, PLoS One, vol. 6, Issue 3, e17968, p. 1-7 (Mar. 23, 2011).
Nina Elisabeth Nagy et al., Effects of Rhizoctonia infection and drought on peroxidase and chitinase activity in Norway spruce (*Picea abies*), Physiologia Plantarum, 120:465-473 (2004).
Dilfuza Egamberdieva et al., High incidence of plant growth-stimulating bacteria associated with the rhizosphere of wheat grown on salinated soil in Uzbekistan, Environmental Microbiology, 10(1), 1-9 (2008).
Randy T. Clark et al., Three-Dimensional Root Phenotyping with a Novel Imaging and Software Platform, Plant Physiology, 156:455-465 (Jun. 2011).
Salme Timmusk et al., The Plant-Growth-Promoting Rhizobacterium Paenibacillus polymyxa Induces Changes in *Arabidopsis thaliana* Gene Expression: A Possible Connection Between Biotic and Abiotic Stress Responses, MPMI, vol. 12, No. 11, pp. 951-959 (Jul. 15, 1999).
Lucian Copolovici et al., Emissions of green leaf volatiles and terpenoids from Solanum lycopersicum are quantitatively related to the severity of cold and heat shock treatments, Journal of Plant Physiology, 169:664-672 (2012).
Galameault, Thomas Paul, A Taxonomic Study of Some Lophotrichous Alcaligenes, Dissertation, Loyola University Chicago, pp. 1-90 (Jun. 1955).
Castillo, Hernández F.D. et al., Biological Control of Root Pathogens by Plant-Growth Promoting *Bacillus* spp., 82 Weed and Pest Control—Conventional and New Challenges, http://dx.doi.org/10.5772/54229, Chapter 4, pp. 1-31 (2013).

* cited by examiner

*Primary Examiner* — Charles Logsdon
(74) *Attorney, Agent, or Firm* — Porter Wright Morris & Arthur LLP

(57) ABSTRACT

A modified *Paenibacillus polymyxa* strain A26, A26ΔSfp, wherein the modified strain A26ΔSfp is incapable of producing enzymatically active 4' phosphopantetheinyl transferase.

17 Claims, 12 Drawing Sheets

Specification includes a Sequence Listing.

A26 wild type

A26Δ*sfp* mutant

RHIZOBACTERIA AND USES THEREOF

The sequence listing submitted herewith, entitled P1113PC00-sequence-listing.txt, created Apr. 6, 2020, and having a size of 2955 bytes, is incorporated herein by reference.

TECHNICAL FIELD

The present embodiments generally relate to rhizobacteria and to uses thereof in improving plant growth, improving stress tolerance of plants and improving nutrient composition in plant substrates.

BACKGROUND

The world population is constantly increasing and it is expected to increase to around 8 billion by the year 2020. In order to feed all of these people, global agricultural productivity must be increased. A key challenge for plant growth is global water shortage, limiting crop yields already today in more than 70% of arable lands. The drought limitations will further gain in importance in the near future as agricultural activities expand to less fertile areas to meet growing demands for food. Accordingly, understanding plant survival and growth under restricted water availability is of central significance in contemporary plant science. A variety of strategies has been used to improve the drought tolerance of crops, including traditional selection methods and genetic engineering. While the traditional methods are slow, there is a certain reluctance of consumers to accept genetically modified plants. In addition, given the large number of different crops with huge variety of cultivars, and the plethora of genes, expression of which need to be altered or novel genes engineered into plants, it is currently unclear whether the engineering technology will develop fast enough to cope with rapidly increasing food demands.

In addition, as a consequence of both environmental and human health concerns, the use of chemical pesticides and fertilizers is increasingly understood to be problematic. To obviate some of these concerns worldwide agricultural practice is moving to a more sustainable and environmental friendly approach. Thus, the amount of organically cultivated land in the western world has increased significantly in recent years. However, in the absence of chemical pesticides and fertilizers, agricultural yields are typically much lower than when they are present. In this context, naturally-occurring soil microorganisms which are living in a thin layer of soil immediately surrounding plant roots known as rhizosphere with beneficial activity on plant growth and health, represent an attractive alternative to conventional agricultural practice. Plant growth in agricultural soils is influenced by many abiotic and biotic factors. These microorganisms facilitate plant growth including water and nutrient uptake, and overcoming a wide range of stresses that the plant experiences. The positive effects that many of these microorganisms have on plants is mediated by a range of mechanisms including improvement of mineral nutrition, enhancement of plant tolerance to biotic and abiotic stress, modification of root development, as well as suppression of soil-borne diseases and soil restoration. The bacterial traits involved in these activities, include biofilm formation, nitrogen fixation, phosphate solubilization, iron sequestration, synthesis of phytohormones, modulation of plant ethylene levels, and control of phytopathogenic microorganisms. Several systems in plants and bacteria are known to have evolved for monitoring the available resources and triggering metabolic, growth, and developmental responses according to the stress situation. In doing so, energy-sensing systems regulate gene expression at multiple levels to allow flexibility in the diversity and the kinetics of the stress response. It is likely that the bacteria together with host plant roots have functioned as a community which, in aggregate, have afforded the plant the adaptability to the harsh conditions encountered.

Document [1] discloses bacteria isolated from the rhizosphere of wild barley *Hordeum spontaneum* and characterizes their 1-aminocyclopropane-1-carboxyale deaminase (ACCd) production, biofilm production, phosphorus solubilization and halophilic behavior.

Document [2] discloses that *Arabidopsis thaliana* plants inoculated with *Paenibacillus polymyxa* were more resistant to both biotic stress (pathogen *Erwinia carotovora*) and abiotic stress (drought) than control plants.

Document [9] discloses inoculant for increasing plant growth, comprising plant growth promoting bacteria of the species *Bacillus subtilis* and *Bacillus thuringiensis*. *B. thuringiensis* strain NEB 17 had plant growth promoting effect when co-inoculated with *Bradyrhizobium japonicum* strain 532C. However, *B. thuringiensis* strain NEB 17 inoculated alone on soybean seedling was not able to form root nodules with soybean, the plants appeared chlorotic and stunted similar to uniincoulated control plants.

Document [10] discloses plant growth enhancing formulations comprising mixtures of microbial isolated. The document states that merely because one strain of microbe may be beneficial to a plant, does not mean that another strain, even of the same species, will provide equal benefits.

Document [11] compares the effect of indigenous drought-tolerant strain of *Glomus intraradices* autochtonous from Mediterranean soil and *G. intraradices* from a collection. The abuscular mycorrhizal fungus were tested alone or in combination with an autochtonous strain of *B. thuringiensis*.

Drought is the major factor for global plant growth limitation. Drought is absence of rainfall or irrigation for a period of time sufficient to deplete soil moisture and injure plants. Drought stress occurs when water is not sufficiently supplied to obtain normal growth of seeds and seedlings and is usually characterized by reduced photosynthesis.

Nutrient availability also increasingly limits plant production. Supplying the soil with nutrients is costly and energy intensive and insufficient supply may result in lower yields and lower nutritional values. At the same time, as a secondary result of climate change, the pathogen attacks to agriculturally important plants are about to increase as well. Furthermore, some pathogens cannot be efficiently limited by chemical control. Hence, the situation challenges us to find practical and sustainable solutions to complex stress situations, i.e. when various stress factors are affecting the plants simultaneously.

Plants weakened by abiotic stress are more susceptible to pathogen attacks resulting in stunted growth or death.

Hence there is a great need for improvements with regard to plant growths and stress tolerance.

SUMMARY

An objective of the embodiments is to provide bacterial strains having beneficial effects to plants.

It is a particular objective of the embodiments to use such bacterial strains in improving plant growth.

It is another particular objective of the embodiments to use such bacterial strains in improving tolerance of plants to various biotic and/or abiotic plant stresses.

These and other objectives are met by embodiments as disclosed herein.

An aspect of the embodiments relates to a *Bacillus thruringiensis* strain AZP2.

Other aspects of the embodiments define a plant substrate comprising AZP2, a plant seed coated with AZP2, a plant root coated with AZP2 and a plant having a plant root coated with AZP2.

Another aspect of the embodiments relates to a bacterial composition comprising AZP2 and at least one of a *Paenibacillus polymyxa* strain A26, an A26 mutant, such as A26Δsfp, and an *Alcaligenes faecalis* strain AF.

Aspects of the embodiments also relate to methods of improving growth of a plant by coating a seed or root of the plant with AZP2 or the above-mentioned bacterial composition or adding AZP2 or the bacterial composition to a plant substrate and then growing the plant seed or root in the plant substrate.

Aspects of the embodiments further relate to methods of improving tolerance of a plant against osmotic stress by coating a seed or root of the plant with AZP2 or the above-mentioned bacterial composition or adding AZP2 or the bacterial composition to a plant substrate and then growing the plant seed or root in the plant substrate.

Another aspect of the embodiment relates to a method of improving nutrient composition of a plant substrate by adding AZP2 or the above-mentioned bacterial composition to the plant substrate.

A further aspect of the embodiments relate to methods of improving plant $P^{3+}$, $K^+$, $Ca^{2+}$ and/or nitrogen contents under stress condition by coating a seed or a root of the plant with AZP2 or the above-mentioned bacterial composition or adding AZP or the bacterial composition to o a plant substrate in which the plant is growing.

Yet another aspect of the embodiments relates to a method of increasing seed germination rate. The method comprises coating a seed of a plant with AZP2 or the above-mentioned bacterial composition.

The *Bacillus thruringiensis* strain AZP2 has several advantageous characteristics that can be used in plant cultivation, agriculture or horticulture. AZP2 can be used for increasing seed germination rate, alleviating plant biotic stress, such as plant pathogens, and abiotic pant stress, such as drought or salt stress and improving plant $P^{3+}$, $K^+$, $Ca^{2+}$ and nitrogen contents under stress conditions. AZP2 also has the effect of improving plant growth under normal conditions as well as restoring soil and enhancing various characteristics of monocot, dicot and tree growth.

The embodiments can therefore be used to increase yield of crop and forestry plants under normal as well as under abiotic and/or biotic stress conditions.

Compared to the use of traditional agronomic practices, i.e. application of fertilizers and pesticides, the embodiments are remarkably less resource and labor intensive, while being environmentally friendly. Hence, they are of practical use for farmers and in particular organic farmers. At the same time they may provide solutions to global environmental problems within the agriculture field, as well as to the challenge of worldwide resource limitation.

BRIEF DESCRIPTION OF THE DRAWINGS

The embodiments, together with further objects and advantages thereof, may best be understood by making reference to the following description taken together with the accompanying drawings, in which.

Values with the same letters in the drawings indicate those that are not statistically different ($P \leq 0.05$ by ANOVA unless otherwise specified).

DETAILED DESCRIPTION

Figure 1:
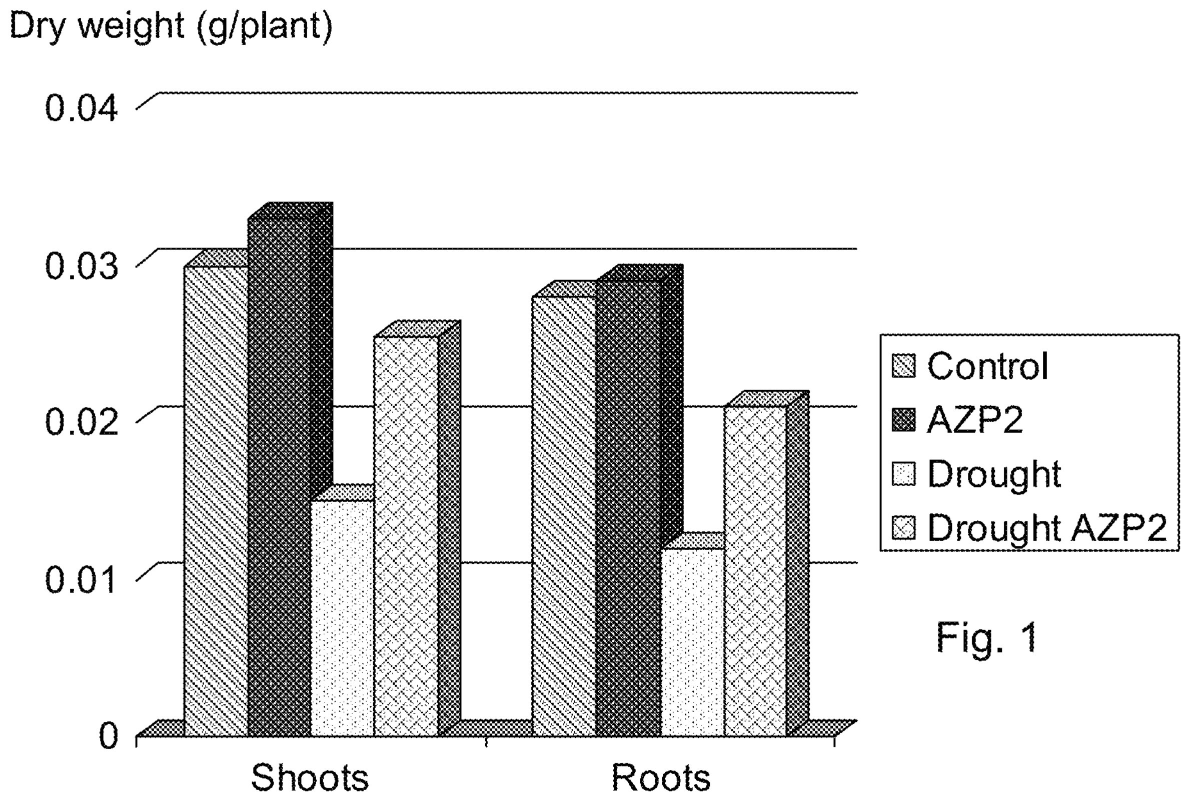
FIG. 1 illustrates the effect of AZP2-priming on wheat (*Triticum aestivum*) dry weight growth in sand and normal watering (control vs. AZP2) and when exposed to drought stress (drought vs. drought AZP2).

The present embodiments generally relate to rhizobacterial strains and uses thereof in plant culturing.

The bacterial strains of the embodiments have, as shown herein, various beneficial effects to plants, including plant growths, plant survival under various abiotic and biotic stress effects and as a general plant soil or substrate improving additive.

An aspect of the embodiment relates to the *Bacillus thuringiensis* strain AZP2.

*B. thuringiensis* is a Gram-positive, soil-dwelling bacterium. This bacterium is today used as a biological pesticide.

It was therefore very surprising that the *B. thuringiensis* strain AZP2 isolated as disclosed herein was a plant growth-promoting bacteria (PGPB) having the capability of improving plant growth in nutrient-deprived plant substrates both under normal watering and when exposed to drought and also improving plant growth under improved nutritional conditions. Furthermore, the strain AZP2 improved the resistance of plants against various agricultural pathogens and was able to improve nutrient composition of plant substrates.

Plants should, herein, be interpreted broadly to include both monocots (monocotyledon) and dicots (dicotyledons) as well as trees.

The *B. thuringiensis* strain AZP2 (generally referred to as AZP2 herein) is obtainable and isolated from *Ponderosa* pine (*Pinus ponderosa*) roots grown on gneiss rock at Mount Lemmon, Ariz., United States of America. In more detail, AZP2 is obtained as a rhizobacterium from the pine roots at latitude and longitude coordinates of N 32° 23.1408' W 110° 41.6315' at an elevation of 2 150 m.

In a particular embodiment, AZP2 is obtainable by a method comprising homogenizing plant rhizosphere material from the above mentioned pine roots to form a bacteria-containing rhizosphere material. The plant rhizosphere material is suspended in a sterile buffer, such as phosphate buffered saline (PBS), to form a plant material suspension. The plant material suspension is optionally heat treated, such as at about 80° C. for about 30 minutes. The optionally heat treated plant material can then be inoculated on culture plates or discs, such as on tryptic soy agar plates. The culture plates may optionally comprise one or more antifungal substances, such as cycloheximide, to prevent or at least reduce fungal growth. Colonies of AZP2 will then form on these culture plates.

The colonies of AZP2 can be tested for their plant drought tolerance enhancement ability as described in experimental section. The isolates able to enhance plant stress tolerance may be chosen for 16S rDNA sequencing from these culture plates.

The optional heat treatment can be used to obtain endospores of AZP2 during the isolation process. Both endospores of AZP2 and vegetative cells can be used in the various uses and methods disclosed herein with equally good results. However, from storage point of view endospores are preferred since they can be stored for unlimited periods of time.

In an embodiment, AZP2 is obtainable and isolated according to the protocol as disclosed in document [1] on pages 2-3 under the section Materials and Methods. The protocol disclosed in this document [1] was used to isolate *Paenibacillus polymyxa* strains but can be used also for the isolation of AZP2 but using the above-mentioned pine roots as starting material instead of wild barley.

AZP2 can easily be grown and propagated in vitro using traditional *Bacillus* culture media and culture conditions. For instance, tryptone soya broth (TSB) medium, luria broth (LB) medium, nutrient broth (NB) medium, peptone dextrose broth (PDB) medium or indeed any other commonly used *Bacillus media, can be employed.*

AZP2 can be long-term stored in glycerol stocks at −80° C. from cultures in the above mentioned media.

AZP2 is an endospore forming siderophore-producing Gram-positive bacterium with AHL-lactonase gene and PlcP global regulator. The biochemical characteristics of AZP2 are listed in Table 1 below.

TABLE 1

Biochemical characteristics of AZP2, A26 and A26Δsfp isolates

| | AZP2 | A26 | A26Δsfp |
|---|---|---|---|
| Carbohydrate metabolsm[1] | | | |
| glycerol | x | x | x |
| L-arbinose | | x | x |
| D-ribose | x | x | x |
| D-xylose | | x | x |
| methyl-bD-xylopyranoside | | x | x |
| D-galactose | | x | x |
| D-glucose | x | x | x |
| D-fructose | x | x | x |
| D-mannose | x | x | x |
| D-mannitol | | x | x |
| methyl-aD-mannopyranoside | | x | |
| methyl-aD-glycopyranoside | | x | x |
| N-acetyl-glycoseamine | x | | |
| amygdaline | | x | x |
| arbutine | x | x | x |
| esculine | x | x | x |
| salicine | x | x | x |
| D-cellobiose | | x | x |
| D-maltose | x | x | x |
| D-lactose (bovine) | | x | x |
| D-melibiose | | x | x |
| D-saccharose | x | x | x |
| D-trehhalose | x | x | x |
| inuline | | x | |
| D-rafinose | | x | x |
| amidon | x | x | x |
| glycogene | x | x | x |
| gentiobiose | | x | x |
| D-turanose | | x | x |
| Idendification test[2] | | | |
| arginine dehydrolase | x | | |
| acetoin production | x | x | x |
| gelatinase | x | | |

[1]Carbohydrate metabolism was studied using the BioMerieux API50CH system following the instructions provided by the manufacturer.

[2]Additional biochemical identification tests were performed using BioMerieux API20E system following the instructions provided by the manufacturer.

For both set of tests bacterial isolates were grown on TSA plates supplied with 2% agar for 18 h. Only positive tests are shown in Table 1. The rest of the API50CH and API20E tests were negative according to the evaluation criteria provided by the manufacturer.

AZP2 has been deposited under depository number MSCL1307 under the Budapest Treaty at the International Depositary Authority (IDA) Microbial Strain Collection of Latvia (MSCL) by the applicant on Aug. 23, 2012.

Another aspect of the embodiments relates to a plant substrate to be used for growing plants. The plant substrate of this embodiment comprises the *B. thuringiensis* strain AZP2. Optionally, the plant substrate may also comprise other rhizobacteria and PGPBs. The plant substrate could be any substrate commonly used for growing plants, including plant seeds, plant roots and plant seedlings. Non-limiting but preferred examples of such plant substrates include soil, peat, compost, vermiculite, perlite, sand or clay.

AZP2, and optionally any other PGPB, can be added to the plant substrate in any possible way. For instance, an aqueous suspension or a culture medium comprising AZP2 could be added to the plant substrate. A further possibility is to add spores of AZP2 to the plant substrate. A further alternative is to add plant material coated or colonized with AZP2 to the plant substrate, such as coated or colonized plant seeds or roots. The spores or AZP2 bacteria could be added to the plant substrate or to the plant seeds or roots in a solution, suspension or medium comprising spores or vegetative AZP2 cells at a concentration of at least $10^3$ bacteria per ml, more preferably at least $10^4$ bacteria per ml, such as at least $10^5$ bacteria per ml or at least $10^6$ bacteria per ml, or more preferably at least about $10^7$ bacteria per ml or even higher concentrations.

A further aspect of the embodiments relates to a plant seed or grain coated or colonized with AZP2. Such a coating of plant seeds with AZP2 can simply be performed by soaking the seeds or grains in a solution, suspension or medium containing AZP2 and optionally at least one other PGPB or as a bacterial inoculum. The solution, suspension or medium preferably comprises AZP2 at a concentration of at least $10^3$ bacteria per ml, more preferably at least $10^4$ bacteria per ml, such as at least $10^5$ bacteria per ml or at least $10^6$ bacteria per ml, or more preferably at least about $10^7$ bacteria per ml or even higher concentrations.

Yet another aspect of the embodiments relates to a plant root coated or colonized with AZP2. Such a coating of plant roots can be performed by growing the plant roots in the above mentioned plant substrate comprising AZP2. Alternatively, or in addition, the plant roots are watered with a solution, suspension or medium containing AZP2. The previously mentioned preferred concentrations of AZP2 in the solution, suspension or medium for seed coating can also be used in connection with plant root coating. The solution, suspension or medium may additionally comprise at least one other PGPB.

A further aspect of the embodiments relates to a plant having a plant root according to the above mentioned aspect, i.e. having at least one of its roots at least partly coated or colonized with AZP2. A related aspect of the embodiments relates to a plant grown from a plant seed coated or colonized with AZP2.

As discussed in the foregoing the plant substrate of the embodiments or the coating of plant seeds or plant roots may comprise at least one additional PGPB or rhizobacterium in addition to AZP2. Particular examples of such PGPB are *Paenibacillus polymyxa* strain A26 as disclosed herein, mutants of A26, such as A26Δsfp, and *Alcaligenes faecalis* strain AF.

*P. polymyxa* is a Gram-positive bacterium used as soil inoculant in agriculture and horticulture. It is believed to be capable of fixing nitrogen.

The *P. polymyxa* strain A26 (generally referred to as A26 herein) is obtainable and isolated from wild barley (*Hordeum spontaneum*) grown at the South Facing Slope, Evolution Canyon, Israel. In more detail, A26 is obtainable as a rhizobacterium from the wild barley roots at latitude and longitude coordinates N 32° 42' 54" E 34° 58' 35" at an elevation of 60 m.

In a particular embodiment, A26 is obtainable by a method comprising homogenizing plant rhizosphere material from the above mentioned wild barley roots to form a bacteria containing rhizosphere material. The plant rhizosphere material is suspended in a sterile buffer, such as PBS, to form a plant material suspension. The plant material suspension is optionally heat treated, such as at about 80° C. for about 30 minutes. The optionally heat treated plant material can then be inoculated on culture plates or discs, such as on tryptic soy agar plates. The culture plates may optionally comprise one or more antifungal substances, such as cycloheximide, to prevent or at least reduce fungal growth. Colonies of A26 will then form on these culture plates.

Colonies of A26 can be tested for their plant drought tolerance enhancement ability as described in the experimental section. The isolates able to enhance plant stress tolerance may be chosen for 16S rDNA sequencing from these culture plates.

The optional heat treatment can be used to obtain endospores of A26 during the isolation process. Both endospores of A26 and vegetative cells can be used in the various uses and methods disclosed herein with equally good results. However, from storage point of view endospores are preferred since they can be stored for unlimited time periods.

In an embodiment, A26 is obtainable and isolated according to the protocol as disclosed in document [1] on pages 2-3 under the section Materials and Methods.

A26 can be cultivated in the same culture media as disclosed above for AZP2 and can stored in glycerol stocks at −80° C. as for AZP2. Biochemical characteristics of A26 are listed in Table 1 above.

A26 is an endospore forming Gram-positive bacterium capable of producing nonribosomal peptide, polyketide, fusaricidin, polymyzin and the polysaccharide levan.

A26 has been deposited under depository number MSCL1306 under the Budapest Treaty at the IDA Microbial Strain Collection of Latvia (MSCL) by the applicant on Aug. 23, 2012.

A26 can be used in wild type form to complement AZP2. A26 exhibits both drought enhancing effect as well as antagonistic effects against pathogens. In particular, addition of the A26 strain specifically strengthens the antagonistic effects in situations with a high number of various pathogens since it broadens the spectrum of antagonism as compared to using AZP2 alone.

A26 may also, or in addition, be used in a mutant form. In particular, an A26 mutant genetically modified to be incapable of producing enzymatically active 4' phosphopantetheinyl transferase Sfp (EC 2.7.8) can be used. The 4' phosphopantetheinyl transferase Sfp transfers 4'-phosphopantetheinyl (Ppant) groups from CoA to conserved serine residues on peptideyl carrier protein (PCP) and acyl carrier protein (ACP) domains in nonribosomal peptide synthetases (NRPS) and polyketide synthetases (PKS) in *P. polymyxa*. The post-translational modification of the PCP and ACP domains with 4'-phsophopantetheyinyl as catalyzed by 4' phosphopantetheinyl transferase Sfp is crucial for the activation of NRPS and PKS.

Nonribosomal peptides produced by NRPS are a very diverse family of natural products with an extremely broad range of biological activities. Examples of biological functions include toxins, siderophores, pigments, antibiotics, cytostatics and immunosuppressors.

Polyketides produced by PKS are structurally a very diverse family of natural products with diverse biological activities. Examples of biological function include antibiotics, antifungals, cytostatics, anticholesteremics, antiparasitics, coccidostats, animal growth promoters and insecticides.

An A26 mutant with inactivated sfp gene is incapable of producing enzymatically active 4' phosphopantetheinyl transferase Sfp, which in turn results in a *P. polymyxa* mutant strain lacking enzymatically active NRPS and PKS. Such an A26 mutant, denoted A26Δsfp herein, has been produced. It was very surprising that this A26Δsfp mutant had the effect of increasing plant dry weight during normal watering condition and in particular when the plant was exposed to drought stress. In addition, the A26Δsfp mutant significantly increased the plant survival during drought stress exposure. Furthermore the A26Δsfp mutant significantly increased A26 biofilm production. The enhanced biofilm production ability of the A26Δsfp mutant implies a great potential to use it as bacterial flocculants.

The genetic modification of A26 to form a mutant strain incapable of producing enzymatically active 4' phosphopantetheinyl transferase Sfp can be achieved in various ways.

In a first approach, the gene encoding 4' phosphopantetheinyl transferase Sfp, i.e. the sfp gene or a homologous gene, can be deleted from the genome of A26. Gene deletion can be in the form of deletion of the complete nucleotide sequence of the gene or at least a portion thereof.

In a second approach at least part of the sfp gene in the genome of A26 is replaced by another nucleotide sequence. Either the complete nucleotide sequence of the gene or a portion thereof is thereby missing in the genetically modified A26.

A third approach is the interruption of the sfp gene by insertion of another nucleotide sequence into the genome of A26 at a position within the gene.

A further approach is based on genetically modifying the nucleotide sequence of the promoter of the sfp gene. For instance, at least one mutation can be introduced into this promoter thereby inactivating the promoter. As a result the transcription of the sfp gene is thereby inhibited. The at least one mutation could, for instance, change the nucleotide sequence of the promoter so that the RNA polymerase is prevented or at least inhibited from recognizing and binding to the mutated promoter sequence. The mutation to the promoter sequence could be performed by deletion of nucleotides of, replacement of nucleotides of or insertion of nucleotides into the promoter sequence.

At least one mutation could alternatively be introduced, such as by site-directed mutation, into the sfp gene. This at least one mutation thereby prevents or inhibits transcription of the sfp gene and/or expression of enzymatically active 4' phosphopantetheinyl transferase Sfp. Hence, the at least one mutation destroys or at least disturbs the gene and/or enzyme function.

A further approach is the introduction of an antisense molecule or sequence complementary to at least a portion of an mRNA transcribed from the sfp gene. This antisense sequence will bind to and thereby prevent or at least inhibit translation of mRNA into 4' phosphopantetheinyl transferase Sfp. The antisense sequence is preferably introduced using a gene cassette comprising a gene sequence encoding the antisense molecule or sequence. The gene cassette preferably comprises a promoter controlling production of the antisense sequence in A26. The gene cassette is preferably incorporated into the genome of A26 or can be provided in A26 but not necessarily incorporated into the genome.

Inactivation of the sfp gene and the genetically modification of A26 to form a mutant incapable of producing an enzymatically active 4' phosphopantetheinyl transferase Sfp can be performed according to any of the above discussed approaches. It is also possible to use multiple, i.e. at least two, of these approaches to produce genetically modified A26.

As stated above, the mutated A26Δsfp strain lacks enzymatically active NRPS and PKS. Hence, it might be possible to achieve the same or similar beneficial effects in terms of increased tolerance to drought stress and/or increased biofilm producing effects of A26Δsfp by producing a mutant A26 strain that is incapable of producing enzymatically active NRPS and/or PKS. Hence, in an alternative approach A26 is genetically modified, such as according to any of the above mentioned approaches, by directing the gene mutation towards the gene(s) encoding NRPS and/or PKS in A26 instead of the sfp gene.

Biochemical characteristics of A26Δsfp are listed in Table 1 above.

The *A. faecalis* strain AF (generally referred to as AF herein) is obtainable and isolated from *Ponderosa* pine (*Pinus ponderosa*) roots grown on gneiss rock at Mount Lemmon, Ariz., United States of America. In more detail, AF is obtained as a rhizobacterium from the pine roots at latitude and longitude coordinates of N 32° 23.1408' W 110° 41.6315' at an elevation of 2 150 m.

In a particular embodiment, AF is obtainable by a method comprising homogenizing plant rhizosphere material from the above mentioned pine roots to form a bacteria-containing rhizosphere material. The plant rhizosphere material is suspended in a sterile buffer, such as PBS, to form a plant material suspension. The plant material suspension is optionally 2 M salt treated, such as at about 24 h. The optionally salt treated plant material can then be inoculated on culture plates or discs, such as on tryptic soy agar plates containing 2 M NaCl. The culture plates may optionally comprise one or more antifungal substances, such as cycloheximide, to prevent or at least reduce fungal growth. Colonies of AF will then form on these culture plates.

The colonies of AF can be tested for their plant drought and salt tolerance enhancement ability as described in experimental section. The isolates able to enhance plant stress tolerance may be chosen for 16S rDNA sequencing from these culture plates.

AF can be cultivated in the same culture media as disclosed above for AZP2 with the exception that it does not grow in peptone dextrose media or in BioMerieux API50 CHB/E medium. It can be stored in glycerol stocks at −80° C.

*A. faecalis* is a Gram-negative obligate aerobe. The bacterium degrades urea, creating ammonia, which increases the pH of the environment. *A. faecalis* has been used for the production of non-standard amino acids.

AF has been deposited under depository number MSCL1394 under the Budapest Treaty at the IDA Microbial Strain Collection of Latvia (MSCL) by the applicant on Aug. 20, 2013.

Another aspect of the embodiments relates to a bacterial composition or combination comprising the *B. thuringiensis* strain AZP2 and at least one of the *P. polymyxa* strain A26, a mutant version of A26 as mentioned above, such as A26Δsfp, and the *A. faecalis* strain AF.

In a first embodiment, the bacterial composition comprises the *B. thuringiensis* strain AZP2 and the *P. polymyxa* strain A26. In a second embodiment, the bacterial composition comprises the *B. thuringiensis* strain AZP2 and a mutant version of the *P. polymyxa* strain A26, such as A26Δsfp. In a third embodiment, the bacterial composition comprises the *B. thuringiensis* strain AZP2 and the *A. faecalis* strain AF. In a fourth embodiment, the bacterial composition comprises the *B. thuringiensis* strain AZP2, the *P. polymyxa* strain A26 and a mutant version of the *P. polymyxa* strain A26, such as A26Δsfp. In a fifth embodiment, the bacterial composition comprises the *B. thuringiensis* strain AZP2, the *P. polymyxa* strain A26 and the *A. faecalis* strain AF. In a sixth embodiment, the bacterial composition comprises the *B. thuringiensis* strain AZP2, a mutant version of the *P. polymyxa* strain A26, such as A26Δsfp and the *A. faecalis* strain AF. In a seventh embodiment, the bacterial composition comprises the *B. thuringiensis* strain AZP2, the *P. polymyxa* strain A26, a mutant version of the *P. polymyxa* strain A26, such as A26Δsfp, and the *A. faecalis* strain AF. In variants of the first to seventh embodiments disclosed above, the bacterial composition comprising at least one other PGPB than the above mentioned PGPBs.

This bacterial composition can then be used to form a plant substrate as previously mentioned and/or for coating plant seeds or plant roots.

The bacterial combinations may be provided as a bacterial solution, a bacterial suspension or indeed in any other form in which the bacteria are viable. For instance, the bacteria can be provided in a culture medium as previously mentioned herein. The bacteria could, as mentioned above, be present as spores and/or as vegetative cells. The concentrations of A26, the A26 mutant and/or AF in the bacterial solution, suspension or medium could be in a same range as previously discussed for AZP2.

A further aspect of the embodiments relates to a method of improving growth of a plant. The method comprises coating a seed of the plant or a root of the plant with AZP2 or AZP2 and at least one other PGPB or rhizobacterium, such as a bacterial composition comprising AZP2 and at least one of A26, an A26 mutant, such as A26Δsfp, and AF. The coated seeds or roots are then grown in a suitable plant substrate.

In another embodiment of this aspect of improving growth of a plant AZP2 either alone or together with at least one other PGPB or rhizobacterium, such as a bacterial composition comprising AZP2 and at least one of A26, an A26 mutant, such as A26Δsfp, and AF, is added to a plant substrate. The plant is then grown in this plant substrate, for instance, by planting a seed or root of the plant in the bacteria enriched plant substrate.

Experimental data as shown herein indicates that AZP2 and indeed A26 and A26Δsfp and AF are capable of increasing the growth of plants when coated plant seeds or roots or added to the plant substrate, or when the bacteria are added to the plant substrate in which the plants are growing. This growth promoting effect is seen both under normal watering conditions in nutrient-deprived plant substrate and nutrient-supplied plant substrate and during drought conditions.

Plant response to a particular type of stress is usually composed of stress-specific adaptive responses, but also of responses that confer unspecific basic protection. The unspecific early signaling events largely determine the capacity of plants to orchestrate a successful adaptive response. This initial basic response involves reestablishing homeostasis, repair damaged cellular components and reprogram metabolism. The AZP2 strain of the embodiments enhances plant-unspecific stress tolerance, hence is especially useful under complex stress situations.

Experimental data presented herein shows that AZP2, A26, A26Δsfp and AF have beneficial effects in improving tolerance of plant against drought stress. Drought stress and salt stress are both osmotic stresses regulated by similar mechanisms in plants. Hence, the bacteria of the embodiments are also beneficial to plants during salt stresses.

An aspect of the embodiments therefore relates to a method of improving tolerance of a plant against osmotic stress, such as drought stress or salt stress as non-limiting examples. The method comprises, in an embodiment, coating a seed or a root of the plant with AZP2 or AZP2 and at least one other PGPB or rhizobacterium, such as a bacterial composition comprising AZP2 and at least one of A26, an A26 mutant, such as A26Δsfp, and AF. Another embodiment of this aspect involves adding AZP2 or AZP2 and at least one other PGPB or rhizobacterium, such as a bacterial composition comprising AZP2 and at least one of A26, an A26 mutant, such as A26Δsfp, and AF, to a plant substrate in which the plant is growing or into which the plant is to be growing or planted.

Experimental data presented herein also indicated that the bacteria of the embodiments have beneficial effects in improving nutrient composition of a plant substrate. A further aspect of the embodiments relates to a method of improving nutrient composition of a plant substrate comprising adding AZP2 or AZP2 and at least one other PGPB or rhizobacterium, such as a bacterial composition comprising AZP2 and at least one of A26, an A26 mutant, such as A26Δsfp, and AF, to the plant substrate.

Experimental data presented herein further indicated that the bacteria of the embodiments have beneficial effects in improving plant content of $P^{3+}$, $K^{+}$, $C^{2+}$ and/or nitrogen under stress condition. Yet another aspect of the embodiments relates to a method of improving plant $P^{3+}$, $K^{+}$, $Ca^{2+}$ and/or nitrogen contents under stress condition comprising coating a seed or a root of the plant with AZP2 or AZP2 and at least one other PGPB or rhizobacterium, such as a bacterial composition comprising AZP2 and at least one of A26, an A26 mutant, such as A26Δsfp, and AF. Another embodiment of this aspect relates to a method of improving plant $P^{3+}$, $K^{+}$, $Ca^{2+}$ and/or nitrogen contents under stress condition comprising adding AZP2 or AZP2 and at least one other PGPB or rhizobacterium, such as a bacterial composition comprising AZP2 and at least one of A26, an A26 mutant, such as A26Δsfp, and AF, to a plant substrate in which the plant is growing.

Experimental data presented herein also indicated that the bacteria of the embodiments have beneficial effects in increasing seed germination rate. A further aspect of the embodiments therefore relate to a method of increasing seed germination rate comprising coating a seed of a plant with AZP2 or AZP2 and at least one other PGPB or rhizobacterium, such as a bacterial composition comprising AZP2 and at least one of A26, an A26 mutant, such as A26Δsfp, and AF.

The bacterial composition of the embodiments may, in a particular embodiment, be formulated for sequential addition of the at least two different rhizobacteria. For instance, the bacterial composition could be formulated as separation solutions, each comprising a respective rhizobacterium. Thus, in such an approach the bacteria strains are configured for addition to a seed of a plant, a root of a plant or a plant substrate dependent on the particular situation and requirement. Under the conditions tested herein it was optimal to have three to seven days between the different bacterial additions. See below Comparison of AZP2, AZP2/A26 and AZP2/AF priming on winter wheat and barley in the example section.

Although generally regarded as being less preferred the bacterial composition could be formulated as a solution comprising the at least two different PGPBs or rhizobacteria. Thus, in such an approach the bacteria strains of the bacterial composition are configured for simultaneous addition to a seed of a plant, a root of a plant or a plant substrate.

In the above disclosed aspects of the embodiments A26, A26 mutants and AF could be used as an additional PGPB to be used together with AZP2. In other aspects of the embodiments, A26 and/or A26 mutants as disclosed herein, such as A26Δsfp, and/or AF could be used as a sole bacterium and optionally together with at least one other PGPB or rhizobacterium. Hence, these other aspects include the *Paenibacillus polymyxa* strain A26, *Paenibacillus polymyxa* strain A26 mutants, such as A26Δsfp, and the *Alcaligenes faecalis* strain AF, a plant substrate comprising A26 and/or an A26 mutant, such as A26Δsfp, and/or AF, a plant seed or plant root coated with A26 and/or an A26 mutant, such as A26Δsfp, and/or AF, and a plant having such a plant root. In addition, these other aspects include methods of improving growth of a plant by coating a seed or a root of a plant with A26 and/or an A26 mutant, such as A26Δsfp, and/or AF and/or adding A26 and/or an A26 mutant, such as A26Δsfp, and/or AF to a plant substrate and then growing the plant seed or root in the plant substrate. Also methods of improving tolerance of a plant against osmotic stress are included by coating a seed or root of a plant with A26 and/or an A26 mutant, such as A26Δsfp, and/or AF and/or adding A26 and/or an A26 mutant, such as A26Δsfp, and/or AF to a plant substrate in which the plant is growing. A method of improving nutrient composition of a plant substrate by adding A26 and/or an A26 mutant, such as A26Δsfp, and/or AF to the plant substrate is included in these other aspects. Also a method of improving plant content of $P^{3+}$, $K^{+}$, $C^{2+}$ and/or nitrogen under stress condition by coating a seed or a root of the plant with A26 and/or an A26 mutant, such as A26Δsfp, and/or AF and/or adding A26 and/or an A26 mutant, such as A26Δsfp, and/or AF to a plant substrate in which the plant is growing is included in these other aspects. These other aspects also encompass a method of increasing seed germination rate comprising coating a seed of a plant with A26 and/or an A26 mutant, such as A26Δsfp, and/or AF.

This means that these additional aspects relates to A26, an A26 mutant, such as A26Δsfp, AF, or a bacterial composition comprising A26 and an A26 mutant, such as A26Δsfp, a bacterial composition comprising A26 and AF, a bacterial composition comprising an A26 mutant, such as A26Δsfp, and AF, a bacterial composition comprising A26, an A26 mutant, such as A26Δsfp, and AF, and uses of these bacteria strains and bacterial compositions as defined above.

The concentration of A26 and/or the mutant A26 and/or AF in these uses could be in a same range as previously disclosed for AZP2.

Figure 9A:
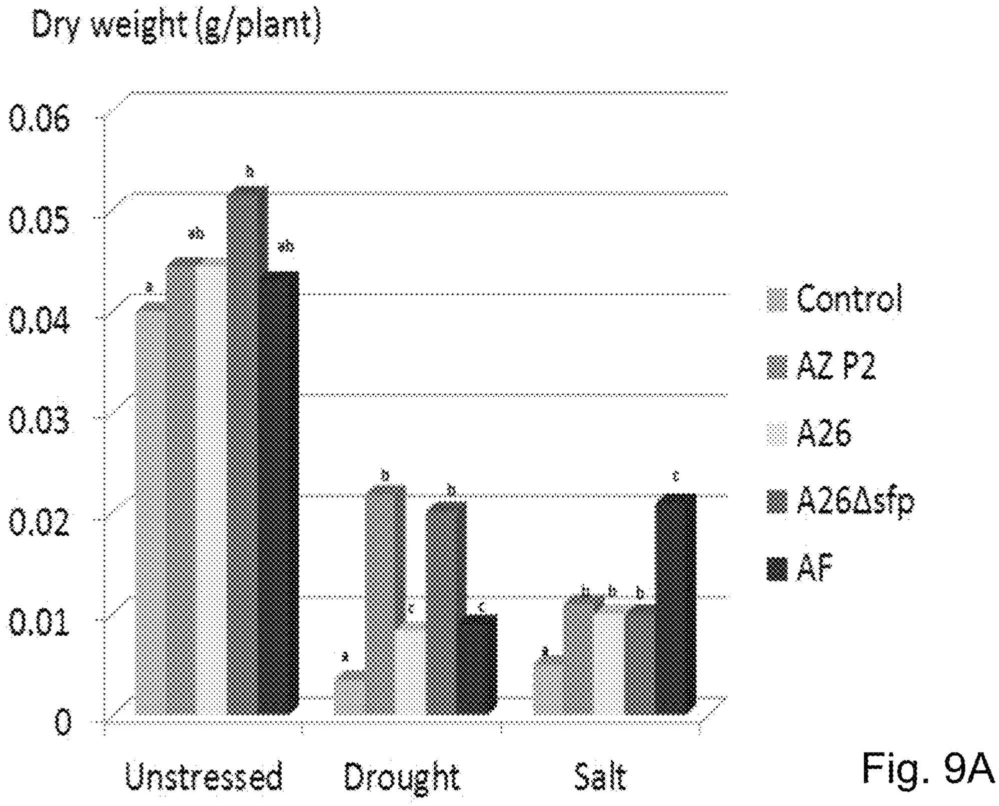
FIGS. 9A and 9B illustrate the comparative effect of AZP2, A26, A26Δsfp and AF on dry weight (FIG. 9A) and survival (FIG. 9B) on winter wheat (cv Stava and Olivin) grown in sand with 10% greenhouse soil and normal watering (unstressed) and exposed to a long drought stress period (drought) and salt stress by watering with 250 mM NaCl.
Figure 9B:
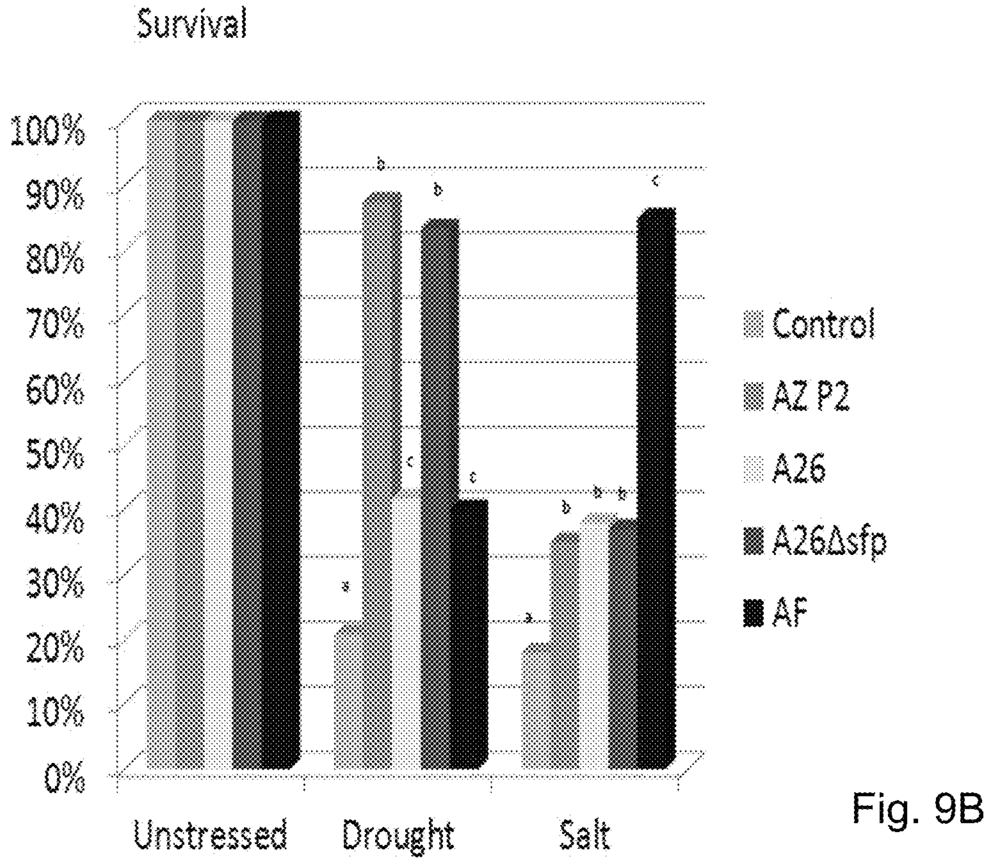

The previously mentioned 4' phosphopantetheinyl transferase Sfp is the phosphopantetheinyl transferase (PPTase) present in Bacillae, Paenibacillae and possibly in *Alcaligenes*. As is shown in FIGS. 9A and 9B inactivating the sfp gene encoding the Sfp PPTase in A26 significantly improved the plant growth promoting effect and drought tolerance of the test plant, winter wheat. It is therefore expected that genetically modifying other rhizobacteria species and strains of Bacillae, Paenibacillae and *Alcaligenes* to produce mutants that are incapable of producing enzymatically active Sfp PPTase or other nonribosomal protein/polyketide (NRPS/PKS) regulators would also have these plant growth and/or drought tolerance promoting effects.

Furthermore, the previously mentioned 4' phosphopantetheinyl transferase Sfp is interfering with bacterial biofilm production ability in Bacillae, Paenibacillae and possibly in *Alcaligenes*. Hence, genetically modified species and strains of Bacillae, Paenibacillae and *Alcaligenes* can be formed with enhanced flocculation ability.

Hence, other aspects of the embodiments relates to a method of generating a Bacillae or Paenibacillae or *Alcaligenes* bacterium having improved plant growth and/or drought tolerance promoting and/or biofilm producing effect. The method comprises genetically modifying the Bacillae or Paenibacillae or *Alcaligenes* bacterium to form a mutant bacterium incapable of producing NRPS/PKS by enzymatically active Sfp PPTase or (an)other gene(s) for NRPS/PKS regulation. The genetic modification preferable comprises inactivating the gene encoding the Sfp PPTase or (an)other gene(s) for NRPS/PKS regulation, for instance using any of the previously discussed approaches. A related aspect defines a Bacillae or Paenibacillae or *Alcaligenes* bacterium genetically modified to be incapable of producing enzymatically active Sfp PPTase or (an)other gene(s) for NRPS/PKS regulation. These aspects also relate to a plant substrate comprising a Bacillae or Paenibacillae or *Alcaligenes* bacterium genetically modified to be incapable of producing enzymatically active Sfp PPTase or (an)other gene(s) for NRPS/PKS regulation, a plant seed or a plant root coated with a Bacillae or Paenibacillae or *Alcaligenes* bacterium genetically modified to be incapable of producing enzymatically active Sfp PPTase or (an)other gene(s) for NRPS/PKS regulation and a plant having such a coated plant root. The Bacillae or Paenibacillae or *Alcaligenes* bacterium genetically modified to be incapable of producing enzymatically active Sfp PPTase can be used in methods of improving growth of a plant, methods of improving tolerance of a plant against osmotic stress and in a method improving nutrient composition of a plant substrate in basically the same way as disclosed above for AZP2, A26, A26Δsfp and AF. In addition, due to the enhanced biofilm production ability, the bacteria incapable of producing enzymatically active Sfp PPTase or other gene for NRPS/PKS regulation can be used in environmental engineering, e.g. water purification.

EXAMPLES

Bacterial Isolation of AZP2

*Bacillus thuringiensis* AZP2 was isolated as a *ponderosa* pine endophytic isolate from *Ponderosa* pine (*Pinus ponderosa*) roots grown on nutrient-deprived gneiss rock at Mt Lemmon, Ariz., USA N 32° 23.1408' W 110° 41.6315' at an elevation of 2 150 m.

The isolation and identification protocols were as disclosed in document [1]. Briefly, the plant roots were carefully shaken and washed in sterile distilled water to remove all loosely attached soil and rock powder and to collect bacteria intimately linked to the plant root. Plants were placed in sterile plastic bags, transferred to the laboratory, and then stored at +4° C. until they were processed in the next day.

Plant rhizosphere material (1 g) was homogenized as described by the manufacturer using FastPrep Instrument (BIO 101® Systems). Hence, the rhizosphere macerate contains bacteria in the endorhizophere.

Plant rhizosphere material was suspended in sterile PBS (137 mM NaCl, 2.7 mM KCl, 10 mM sodium phosphate dibasic, 2 mM potassium phosphate monobasic, pH of 7.4).

The content of endospore-forming bacteria was determined after heat treatment of the plant material suspension at 80° C. for 30 min. Tryptic Soy Agar (TSA) plates were inoculated with 100 μL of these suspensions, corresponding to $10^{-3}$-$10^{-5}$ g plant rhizosphere material per plate. All agar media contained 15 g agar and 50 mg cycloheximide, to reduce fungal growth, and had a pH of 7. The inoculated petri dishes were incubated for several weeks at 30° C. in boxes together with a beaker of water (to prevent drying of the agar).

The colonies for the endospore forming bacteria were studied for plant drought stress tolerance enhancement and the efficient strains were identified by 16S rDNA sequencing.

AZP2-Priming of Wheat—Dry Weight Assessment

The seeds of spring wheat (*Triticum aestivum* L. cv. Sids1, Stava and Olivin) were used to assess drought stress tolerance enhancing effect of the *Bacillus thuringiensis* strain AZP2. The seeds were surface sterilized with 5% chlorine solution. The bacteria were grown in Tryptone Soy Broth (TSB) medium at 28° C. overnight. Culture density was determined by colony forming unit analysis (CFU). Priming was performed by soaking grains in solutions containing $10^7$ bacteria $ml^{-1}$ for 4 hours at 28° C. For the control treatment, another set of grains was soaked in sterile TSB media. Grains were planted in sand soil and left to grow in controlled environment in a MLR-351H (Phanasonic, Ill., USA) growth chamber with 24/16° C. (day/night) temperature, and 16 h photoperiods at 250 μmol $m^{-2}$ $s^{-1}$ and 60% humidity. Plants were watered daily for 10 days. For drought stress treatment, 10-days-old plants were left to grow without water for 10 days.

FIG. 1 illustrates the effect of AZP2-priming on wheat (*Triticum aestivum*) dry weight grown in sand without water for 10 days. Shoot and root dry weight of 8 independent experiments is shown. The last two columns of each column set represent plants exposed to drought stress in the absence and presence of AZP2.

Wheat seeds treated with AZP2 created about 9% higher growth of shoots when grown in nutritionally poor soils and normal watering regime (AZP2 vs. Control in FIG. 1). A slight increase was also seen for the dry weight of the wheat roots. Under drought stress the AZP2-treated plants had significantly larger shoot and root dry weights (Drought AZP2 vs. Drought in FIG. 1), with a dry weight increase of about 78%.

AZP2-Priming on *Arabidposis thaliana*—Dry Weight Assessment

*A. thaliana* seeds were surface-sterilized using 5% chlorine solution and grown for 2 weeks in Murashige-Skoog (MS) medium. Subsequently, the seedlings were planted in peat and let to grow for 7 more days. Bacteria were grown in TSB medium at 28° C. overnight. Culture density was determined by CFU. Priming was performed by watering seedlings with 10 ml solutions containing $10^7$ bacteria $ml^{-1}$. For the control treatment, another set of grains was watered with diluted sterile TSB media.

Figure 2:
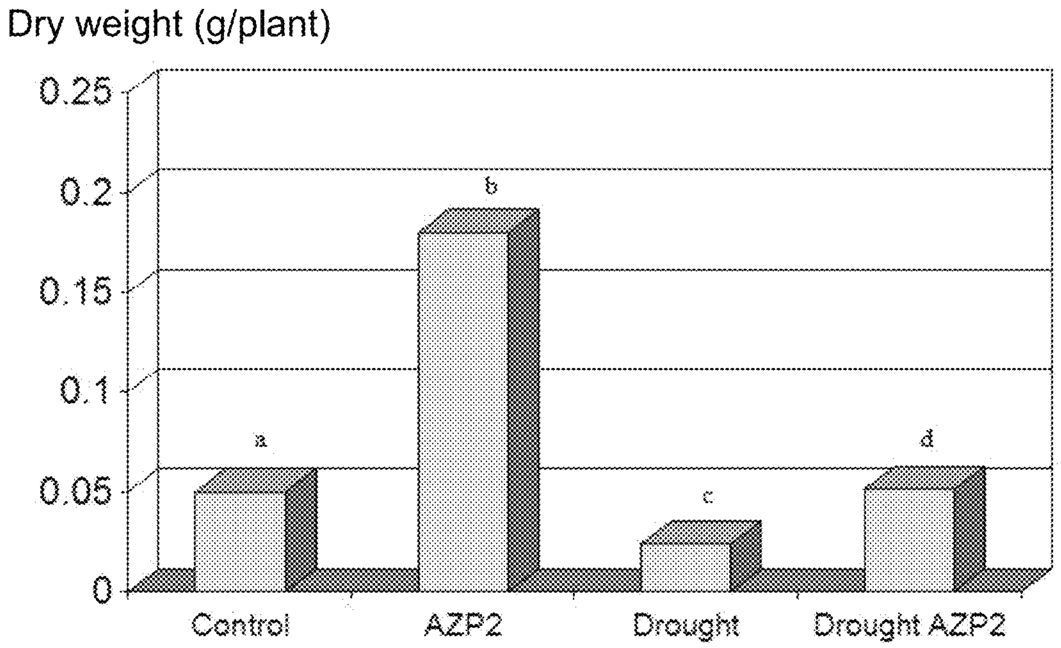
FIG. 2 illustrates the effect of AZP2-priming on *Arabidopsis thaliana* dry weight of five week old seedlings grown in peat and normal watering (control vs. AZP2) and when exposed to drought stress (drought vs. drought AZP2).

FIG. 2 illustrates the effect of AZP2-priming on *A. thaliana* dry weight of five week old seedlings grown in peat under exposure to drought stress for 14 days. Plant dry weights of 8 independent experiments are shown. This shows that AZP2 inoculation significantly promotes plant growth under normal water conditions as well as enhances plant drought stress tolerance. AZP2-priming was in this case able to significantly increase the dry weight both in nutritionally poor soil but normal watering (210% increase over control) and in nutritionally poor soil with drought stress (100% increase over control).

AZP2-Priming on Scots Pine—Dry Weight Assessment

Scots pine (*Pinus sylvestris*) seeds were surface-sterilized using 5% chlorine solution and germinated on water agar for 3 weeks. Subsequently seedlings were planted in sand soil mixed with 10% greenhouse soil and let to grow one more week. Bacteria were grown in TSB medium at 28° C. overnight. Culture density was determined by CFU. Priming was performed by watering seedlings with 10 ml solutions containing $10^7$ bacteria $ml^{-1}$. For the control treatment, another set of grains was watered with diluted sterile TSB media.

Figure 3:
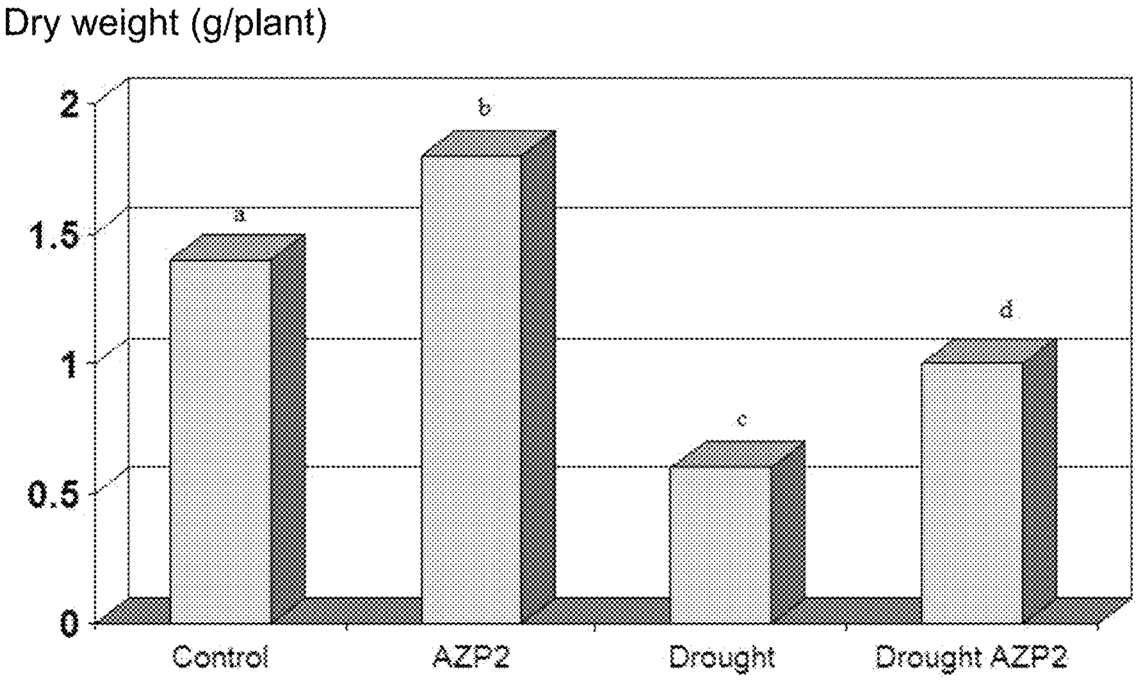
FIG. 3 illustrates the effect of AZP2-priming on Scots pine (*Pinus sylvestris*) dry weight of five week old seedlings with normal watering (control vs. AZP2) and when exposed to drought stress (drought vs. drought AZP2).

FIG. 3 illustrates the effect of AZP2-priming on Scots pine dry weight of five week old seedlings grown under exposure to drought stress for 30 days. AZP2-priming increased the dry weight both in nutritionally poor soil but normal watering (28% increase over control) and in nutritionally poor soil with drought stress (67% increase over control).

AZP2-Priming of Wheat—Survival Assessment

Figure 4:
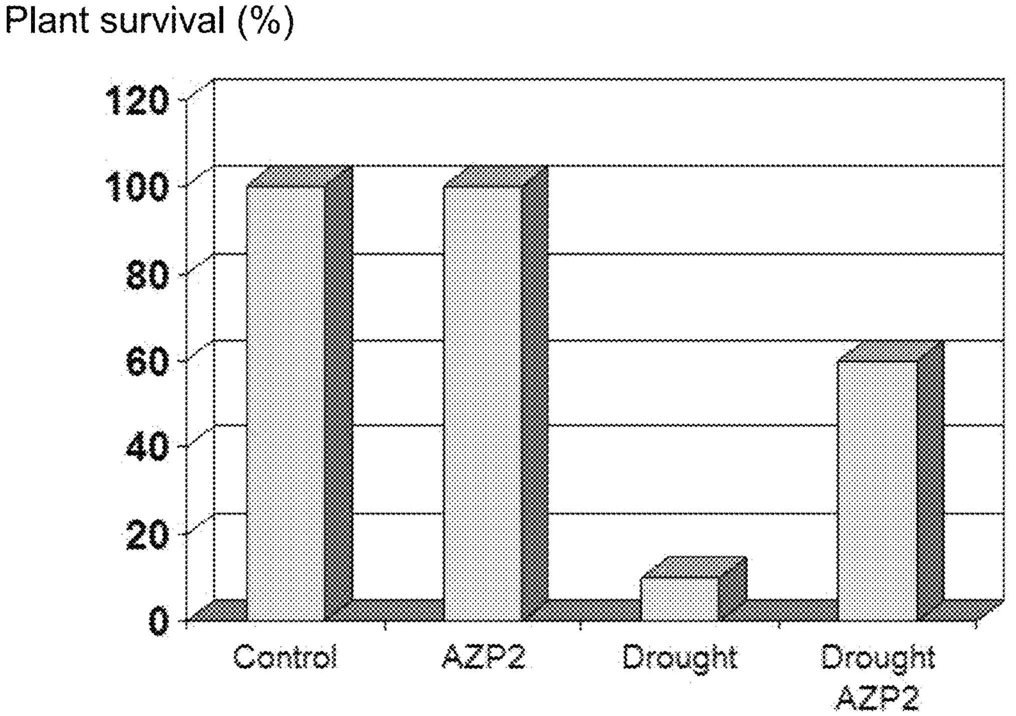
FIG. 4 illustrates the effect of AZP2-priming on wheat (*Triticum aestivum*) survival during normal watering (control vs. AZP2) and when exposed to drought stress (drought vs. drought AZP2).

FIG. 4 illustrates the effect of AZP2-priming on the survival of wheat seedlings grown without water for 8 days. AZP2-primed ($10^7$ bacteria $ml^{-1}$) plant survival was compared to untreated controls using 32 stressed plants that were randomly selected and divided into two groups with 16 plants each. Plants were watered and allowed to recover for 4 days. The recovered plants were counted as survived plants. Growth parameters for both shoots and roots were determined after 7 days drought stress. The plants were harvested, washed and dried between two filter papers. Fresh mass was determined before the samples were dried at 50° C. till constant mass. As shown in the figure both control plants and AZP2-treated plants had a survival rate of 100% under normal watering condition (Control vs. AZP2). However, during the drought stress almost none of the untreated plants (Drought) survived whereas about 60% of the AZP2-primed plants (Drought AZP2) survived the drought stress. AZP2-priming resulted in a 500% increase in survival as compared to control when exposed to drought conditions.

AZP2-Priming on *Arabidposis thaliana*—Survival Assessment

Figure 5:
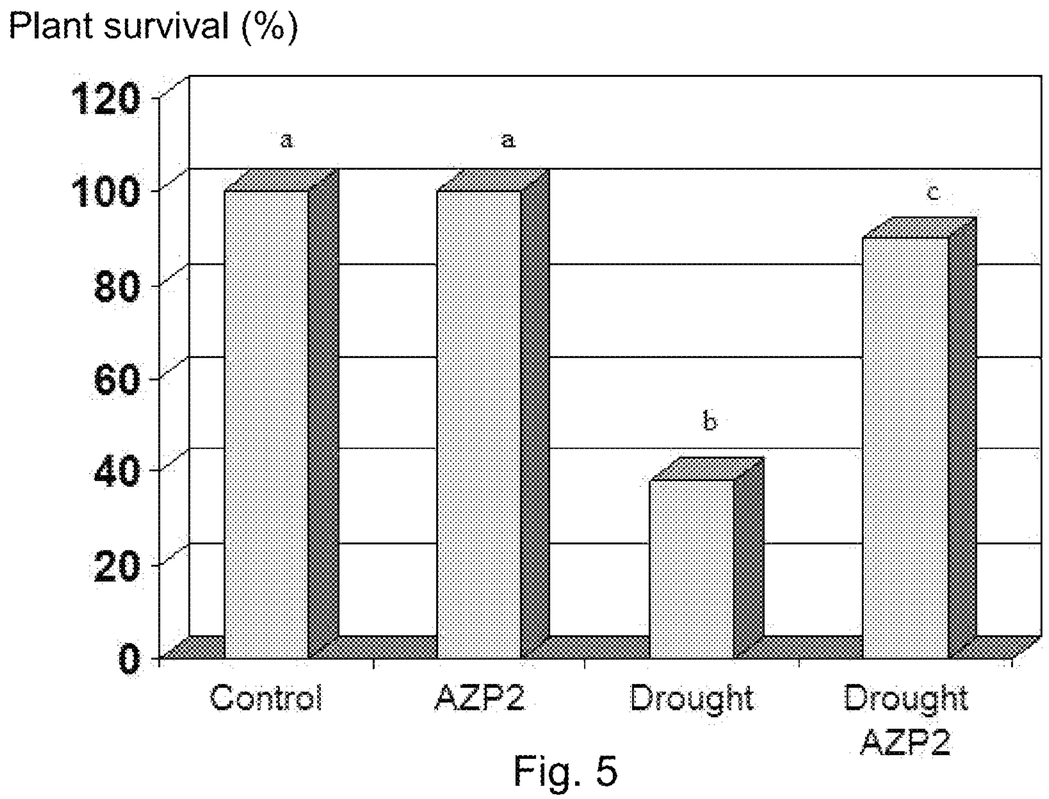
FIG. 5 illustrates the effect of AZP2-priming on *Arabidopsis thaliana* dry survival during normal watering (control vs. AZP2) and when exposed to drought stress (drought vs. drought AZP2).

FIG. 5 illustrates the effect of AZP2-priming on the survival of *A. thaliana* grown without water for 14 days. AZP2-primed ($10^7$ bacteria $ml^{-1}$) plant survival was calculated using 32 stressed plants that were randomly selected and divided into two groups with 16 plants each. Plants were watered and allowed to recover for 4 days. The recovered plants were counted as survived plants. Growth parameters for both shoots and roots were determined after 14 days drought stress. The plants were harvested, washed and dried between two filter papers. Fresh mass was determined before the samples were dried at 50° C. till constant mass. As shown in the figure both control plants and AZP2-treated plants had a survival rate of 100% under normal watering condition (Control vs. AZP2). However, during the drought stress less than 40% of the untreated plants (Drought) survived whereas over 80% of the AZP2-primed plants (Drought AZP2) survived the drought stress. AZP2-priming resulted in a 100% increase in survival as compared to control when exposed to drought conditions.

AZP2-Priming on Scots Pine—Survival Assessment

Figure 6:
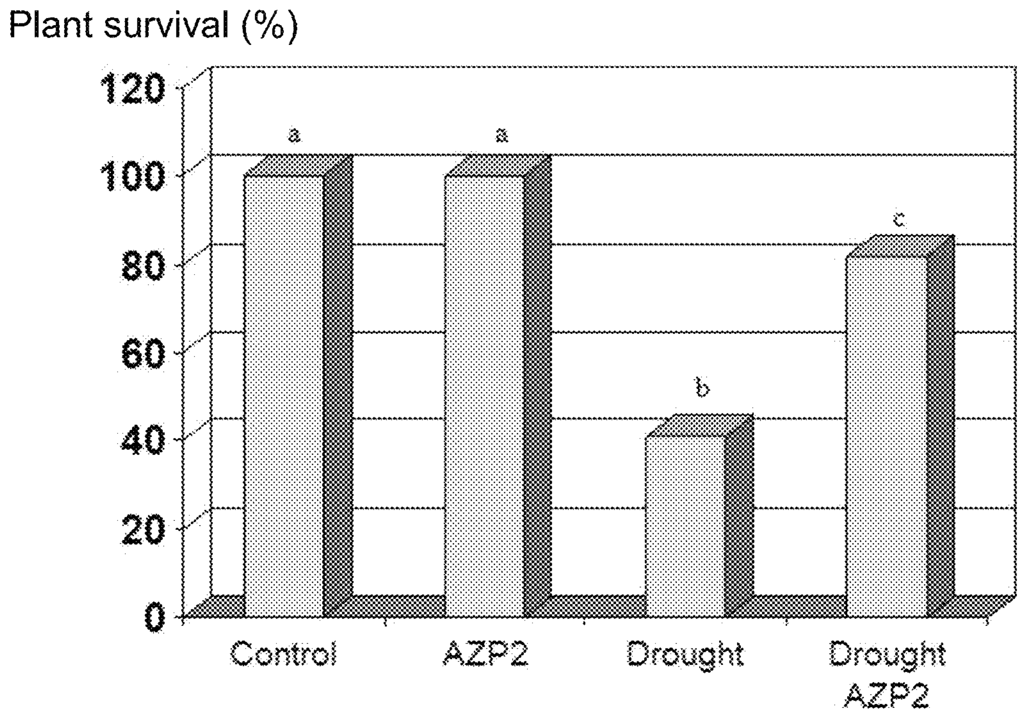
FIG. 6 illustrates the effect of AZP2-priming on Scots pine (*Pinus sylvestris*) survival during normal watering (control vs. AZP2) and when exposed to drought stress (drought vs. drought AZP2).

FIG. 6 illustrates the effect of AZP2-priming on the survival of Scots pine grown without water for 30 days. AZP2-primed ($10^7$ bacteria $ml^{-1}$) plant survival was calculated using 32 stressed plants that were randomly selected and divided into two groups with 16 plants each. Plants were watered and allowed to recover for 4 days. The recovered plants were counted as survived plants. Growth parameters for both shoots and roots were determined after 30 days drought stress. The plants were harvested, washed and dried between two filter papers. Fresh mass was determined before the samples were dried at 50° C. till constant mass. As shown in the figure both control plants and AZP2-treated plants had a survival rate of 100% under normal watering condition (Control vs. AZP2). However, during the drought stress about 40% of the untreated plants (Drought) survived whereas over 80% of the AZP2-primed plants (Drought AZP2) survived the drought stress. AZP2-priming resulted in a 100% increase in survival as compared to control when exposed to drought conditions.

Table 2 below summaries the improvements of achieved by AZP2-priming on plant biomass under nutritionally poor soil and drought stress.

Bacterial Isolation of A26

*Paenibacillus polymyxa* A26 strain was isolated from the rhizosphere of wild barley (*Hordeum spontaneum*) at South Facing Slope, Evolution Canyon, Israel, N 32° 42' 54" E 34° 58' 35" at an elevation of 60 m. The isolation and identification protocols were as disclosed in [1]. Briefly, the plant roots were carefully shaken and washed in sterile distilled water to remove all loosely attached soil and rock powder and to collect bacteria intimately linked to the plant root. Plants were placed in sterile plastic bags, transferred to the laboratory, and then stored at +4° C. until they were processed in the next day. Plant rhizosphere material (1 g) was homogenized as described by the manufacturer using Fast-Prep Instrument (BIO 101® Systems). Hence, the rhizosphere macerate contains bacteria in the endorhizophere. Plant rhizosphere material was suspended in sterile PBS (137 mM NaCl, 2.7 mM KCl, 10 mM sodium phosphate dibasic, 2 mM potassium phosphate monobasic, pH of 7.4).

TABLE 2 summary of effects by AZP2-priming of plants

| | Increase over control | | | | | | | | |
|---|---|---|---|---|---|---|---|---|---|
| | Nutritionally poor soil, normal watering | | | Nutritionally poor soil - drought stress | | | | | |
| | Dry weight increase % | | | Dry weight increase % | | | Survival increase % | | |
| | AZP2 | AZP2 + A26 | AZP2 + AF | AZP2 | AZP2 + A26 | AZP2 + AF | AZP2 | AZP2 + A26 | AZP2 + AF |
| Wheat | 9 | 20 | 10 | 78 | 100 | 85 | 500 | 575 | 550 |
| Barley | 8 | 20 | 9 | 76 | 100 | 86 | 500 | 570 | 540 |
| *A. thaliana* | 20 | | | 100 | | | 100 | | |
| Scots pine | 28 | | | 67 | | | 100 | | |

Effect of AZP2-Priming on Photosynthesis

A plant usually responds to osmotic stress, such as drought stress, by repressed growth and/or photosynthesis. The effects of AZP2-priming on wheat were therefore investigated. AZP2-priming of wheat was performed as disclosed above under AZP2-priming of wheat—dry weight assessment. Two photosynthetic parameters, net assimilation and stomatal conductance (002 taken up from the air through the stomata), were selected to quantify the degree of photosynthesis of a plant.

Figure 7A:
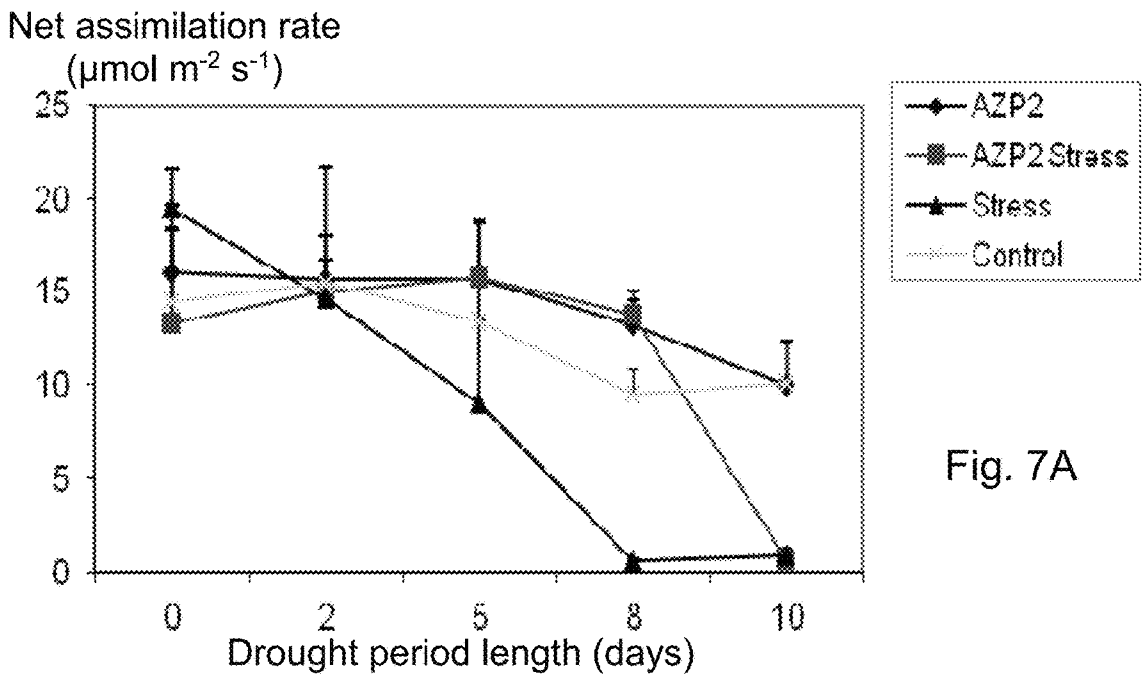
FIGS. 7A and 7B illustrate the effect of AZP2-priming on the photosynthetic parameters stomatal conductance (FIG. 7A) and net assimilation (FIG. 7B) in wheat during normal watering (control vs. AZP2) and when exposed to drought stress (stress vs. AZP2 stress).
Figure 7B:
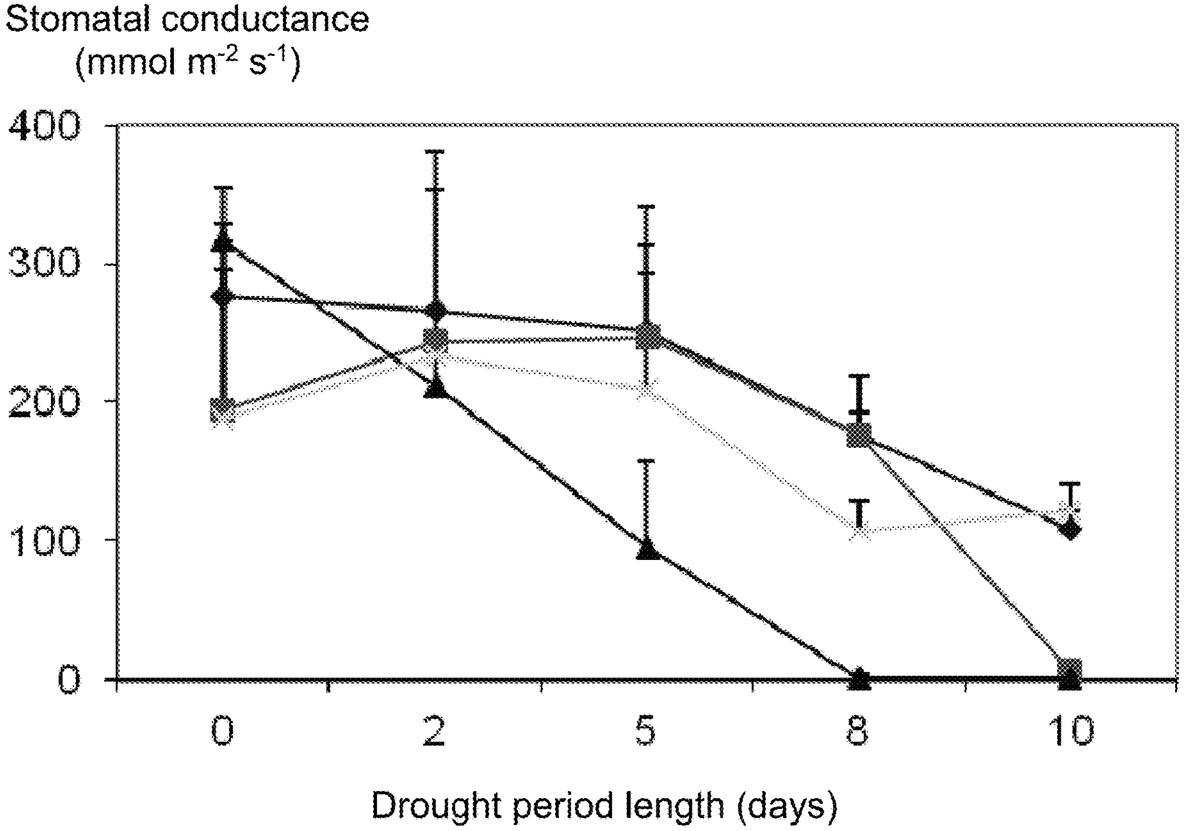

Two week old wheat plantlets were exposed to drought stress for 10 days. FIGS. 7A and 7B illustrate the result of stomatal conductance (FIG. 7A) and net assimilation (FIG. 7B) under normal water conditions (Control vs. AZP2) and during drought stress (Stress vs. AZP2 stress). Error bars indicate differences between three independent controls. Net assimilation rate and stomatal conductance were recorded immediately after stress application (day 0) and in 2, 5, 8 and 10 days from stress application using GFS-3000 portable Gas Exchange System equipped with a leaf chamber fluorimeter (H. Walz GmbH, Effeltrich, Germany) [3]. Leaf temperature was set at 25° C., incident quantum flux density at 1000 μmol $m^{-2}$ $s^{-1}$, chamber $CO_2$ concentration at 390 μmol $mol^{-1}$ and air humidity at 60%.

The stomatal conductance and net assimilation represent good quantitative measures for showing improved photosynthesis and plant vitality of AZP2-primed plants. As illustrated in FIGS. 7A and 7B AZP2-priming improved drought stress tolerance through upheld photosynthesis.

The content of endospore-forming bacteria was determined after heat treatment of the soil or plant material suspension at 80° C. for 30 min. Tryptic Soy Agar (TSA) plates were inoculated with 100 μL of these suspensions, corresponding to $10^{-3}$-$10^{-5}$ g soil or plant rhizosphere material per plate. All agar media contained 15 g agar and 50 mg cycloheximide, to reduce fungal growth, and had a pH of 7. The inoculated petri dishes were incubated for several weeks at 30° C.

The colonies for the endospore forming bacteria were studied for plant drought stress tolerance enhancement and the efficient strains were identified by 16S rDNA sequencing.

Gene Inactivation in A26

Rhizobacterially-produced nonribosomal peptides and polyketides are biologically active products of the reactions catalyzed by nonribosomal peptide synthetase (NRPS) and polyketide synthetases (PKS). PKS is a multi-domain enzyme containing numerous enzymatic domains organized into functional units. PKS catalyzes production of polyketides (PK), which is a large class of secondary metabolites. Correspondingly, NRPS are large multifunctional enzymes synthesizing nonribosomal peptides (NRP), which is a class of peptide secondary metabolites having an extremely broad range of biological activities.

The vast structural diversity of these enzymes is due to a wide range of available substrates compared to the mere 20 amino acids available for ribosomal synthesis. Despite the enormous chemical diversity the PKS and NRPS share a common point of regulation. All of these enzymes require activation by 4'-phosphopantetheinyl transferase (PPTase).

In Bacillae, Paenibacillae and possibly in *Alcaligenes* the PPTase is 4' phosphopantetheinyl transferase Sfp. 4' phosphopantetheinyl transferase Sfp transfers 4'-phosphopantetheinyl (Ppant) groups from CoA to conserved serine residues on peptideyl carrier protein (PCP) and acyl carrier protein (ACP) domains in NRPSs and PKSs. The post-translation modification of PCP and ACP domains by 4-phosphopantetheinyl is crucial for the activation of NRPS and PKS. This reaction is catalyzed by phosphopantetheinyl transferases (PPTase), such as 4' phosphopantetheinyl transferase Sfp.

The sfp gene of A26 was inactivated and the sfp gene inactivation resulted in an A26 mutant (A26Δsfp) unable to produce NRPS and PKS.

742 bp and 794 bp fragments of the flanking regions of the sfp gene in A26 were amplified by PCR from the A26 chromosomal DNA using the sfp FF and sfp FR primer pair and the sfp RF and sfp RR primer pair, respectively, resulting in the PCR products: upstream fragment and downstream fragment respectively.

```
sfp FF:
                                        (SEQ ID NO: 1)
5'-CTC ATG CAT CAT TGT AAA TCA CTT TCG GAC G-3'

sfp FR:
                                        (SEQ ID NO: 2)
5'-CTC GGA TCC TCT TAA CAG CAC ATC GGC AT-3'

sfp RF:
                                        (SEQ ID NO: 3)
5'-CTC TCT AGA GAA GTC TTT TTC ATT CGA GCT-3'

sfp RR:
                                        (SEQ ID NO: 4)
5'-CTC GGG CCC TAA TCC GTT CAA GCG TCC AT-3'
```

The pGEM7Z (Promega) vector was used in the experiment. A chloramphenicol resistance marker gene was cloned into the vector using the EcoRI-BamHI site to form the vector pGEM7Z/Cm. The upstream fragment was cloned into the pGEM7Z/Cm vector using NsiI and BamHI site. Thereafter the downstream fragment was cloned in to the pGEM7Z/Cm vector using XbaI and ApaI restriction enzymes.

The final pGEM7Z/Cm vector was transformed into *P. polymyxa* A26 as follows. The day before the experiment, a single colony of *P. polymyxa* on TSA plate was inoculated in BHIS (Brain heart infusion-Difco and 10% sucrose) and cultivated at 30° C. and 200 rpm. Two mL of pre-culture were inoculated in 200 mL of BHIS and cultured at 30° C. When the cells reached an $OD_{600}$ of 0.5, the culture was cooled on ice for 10 min. Bacterial cells were centrifuged at 7000 rpm for 10 min at 4° C. The supernatant was discarded and the pellet resuspended with pre-cold SM buffer (10% sucrose and 1 mM $MgCl_2$) with equal volume. The pellet was washed with SM buffer. Finally, the pellet was resuspended in SM buffer with 1/100 volume. Electroporation was performed using a Gene Pulser (Bio-Rad Laboratories). The competent A26 cells were thawed on ice, mixed with the pGEM7Z/Cm vector, transferred to 2 mm cuvettes, and placed on ice for at least 5 min. The sample was pulsed with a voltage of 0.25 kV $cm^{-1}$, a capacitance of 25 μF, and a resistance of 200Ω. One mL of pre-warmed BHIS was added and incubated at 30° C. for 3 h. After incubation, the cells were cultured on TSA plates containing Cm restriction marker.

Figure 8:
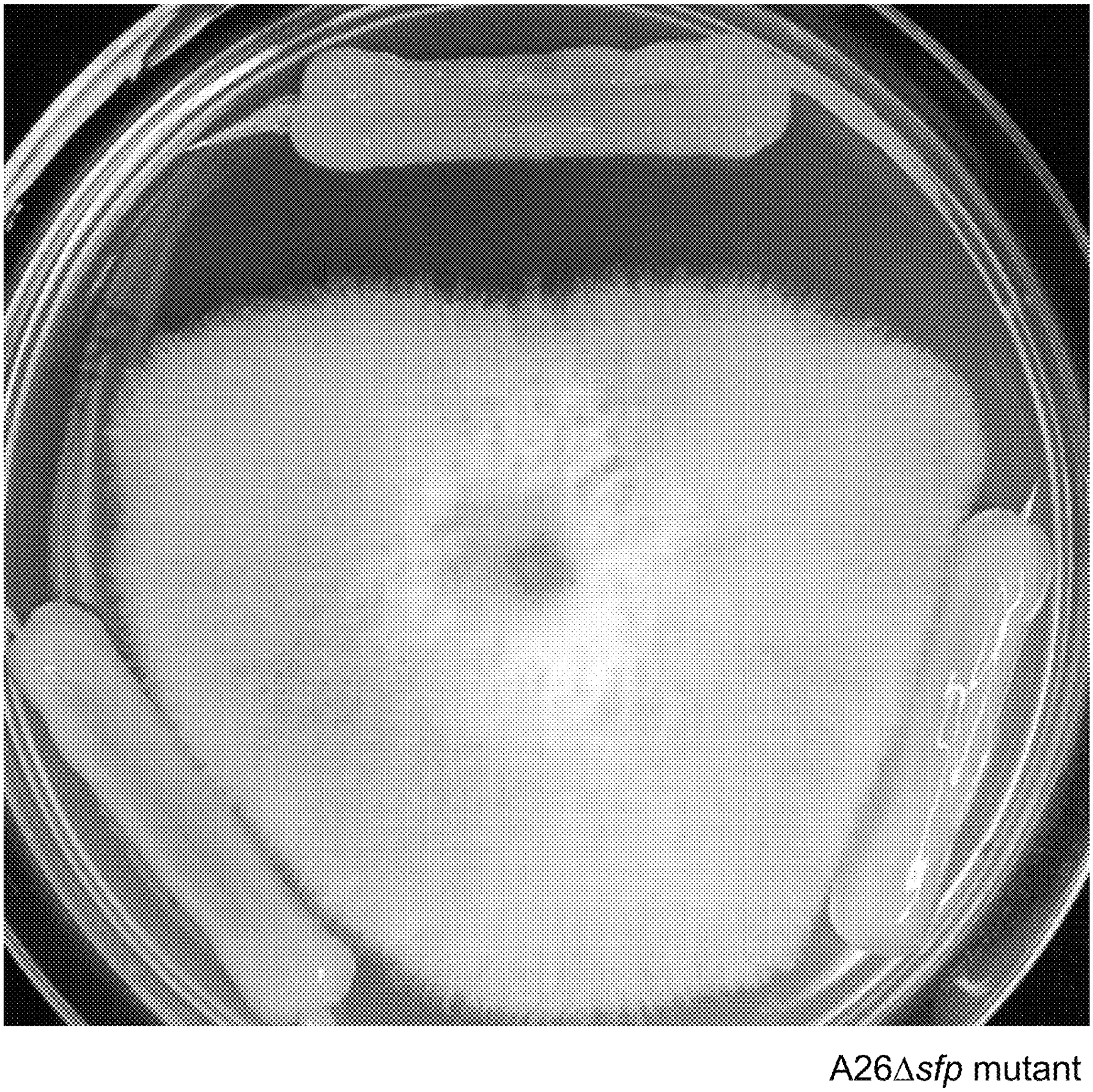
FIG. 8 illustrates a culture plate confirming A26 sfp inactivation.

FIG. 8 illustrates a plate assay showing A26 sfp inactivation. The antagonist activity of wild type A26 and the A26Δsfp mutant against *Fusarium avenaceum*. Fusaricidins are nonribosomally produced antibiotics efficiently antagonizing *Fusarium* spp. (here used as positive control). Note that an antagonistic zone is missing for the mutant, thereby confirming loss of NRP/PK synthesis of the A26Δsfp mutant Bacterial Isolation of AF

*Alcaligenes faecalis* AF was isolated as a *ponderosa* pine endophytic isolate from *Ponderosa* pine (*Pinus ponderosa*) roots grown on nutrient-deprived gneiss rock at Mt Lemmon, Ariz., USA N 32° 23.1408' W 110° 41.6315' at an elevation of 2 150 m.

The Isolation and Identification Protocols were as Disclosed in Document [1] was Slightly Modified. Briefly, the plant roots were carefully shaken and washed in sterile distilled water to remove all loosely attached soil and rock powder and to collect bacteria intimately linked to the plant root. Plants were placed in sterile plastic bags, transferred to the laboratory, and then stored at +4° C. until they were processed in the next day.

Plant rhizosphere material (1 g) was homogenized as described by the manufacturer using FastPrep Instrument (BIO 101® Systems). Hence, the rhizosphere macerate contains bacteria in the endorhizophere.

Plant rhizosphere material was suspended in sterile PBS (137 mM NaCl, 2.7 mM KCl, 10 mM sodium phosphate dibasic, 2 mM potassium phosphate monobasic, pH of 7.4).

The rhizosphere suspension was then salt treated with TSB containing 2 M NaCl for 24 h. Tryptic Soy Agar (TSA) plates containing 2 M NaCl were inoculated with 100 μL of these suspensions, corresponding to $10^{-3}$-$10^{-5}$ g plant rhizosphere material per plate. All agar media contained 15 g agar and 50 mg cycloheximide, to reduce fungal growth, and had a pH of 7. The inoculated petri dishes were incubated for several weeks at 30° C. in boxes together with a beaker of water (to prevent drying of the agar).

The colonies for the endospore forming bacteria were studied for plant drought and salt stress tolerance enhancement and the efficient strains were identified by 16S rDNA sequencing using 27F primer AGAGTTTGATCMTGGCTCAG (SEQ ID NO: 5).

*A. faecalis* 16S rDNA sequence is provided below and in SEQ ID NO: 6:

```
GGGCAATCCGGGCAGCCTTTAACATGCAAGTTCGAACGGCAGCGCGAGAGA
GCTTGCTCTCTTGGCGGCGAGTGGCGGACGGGTGAGTAATATATCGGAACG
TGCCCAGTAGCGGGGGATAACTACTCGAAAGAGTGGCTAATACCGCATACG
CCCTACGGGGGAAAGGGGGGGATCGCAAGACCTCTCACTATTGGAGCGGCC
GATATCGGATTAGCTAGTTGGTGGGGTAAAGGCTCACCAAGGCAACGATCC
GTAGCTGGTTTGAGAGGACGACCAGCCACACTGGGACTGAGACACGGCCCA
GACTCCTACGGGAGGCAGCAGTGGGGAATTTTGGACAATGGGGGAAACCCT
GATCCAGCCATCCCGCGTGTATGATGAAGGCCTTCGGGTTGTAAAGTACTT
TTGGCAGAGAAGAAAAGGTATCCCCTAATACGGGATACTGCTGACGGTATC
TGCAGAATAAGCACCGGCTAACTACGTGCCAGCAGCCGCGGTAATACGTAG
GGTGCAAGCGTTAATCGGAATTACTGGGCGTAAAGCGTGTGTAGGCGGTTC
GGAAAGAAAGATGTGAAATCCCAGGGCTCAACCTTGGAACTGCATTTTTAA
CTGCCGAGCTAGAGTATGTCAGAGGGGGGTAGAATTCCACGTGTAGCAGTG
AAATGCGTAGATATGTGGAGGAATACCGATGGCGAAGGCAGCCCCCTGGGA
```

-continued

```
TAATACTGACGCTCAGACACGAAAGCGTGGGGAGCAAACAGGATTAGATAC

CCTGGTAGTCCACGCCCTAAACGATGTCAACTAGCTGTTGGGGCCGTTAGG

CCTTAGTAGCGCAGCTAACGCGTGAAGTTGACCGCCTGGGGAGTACGGTCG

CAAGATTAAACTCAGGAAATGGCG.
```

Comparison of AZP2, A26, A26Δsfp and AF Priming on Winter Wheat

Comparative effect of AZP2, A26, A26Δsfp and AF priming on survival and dry weights of winter wheat (cv Stava and Olivin) grown under slightly improved nutritional conditions (sand with 10% greenhouse soil) and exposed to longer drought stress and salt stress period was investigated. Dry weight experiments were performed after 20 days and survival after 14 days of drought or salt exposure. For salt stress plants were watered with 250 mM salt stress solution. Note that A26Δsfp improved plant dry weight by 27% under no stress exposure, see FIG. 9A. AZP2 and A26Δsfp improved plant dry weight under drought stress about 600%, see FIG. 9A. AZP2 and A26Δsfp primed plant survival was 4 times higher compared to controls after 14 days of drought stress, see FIG. 9B.

Thus, mutation of A26 by inactivating, i.e. knocking-out, the sfp gene dramatically improved the drought stress tolerance of wheat primed by A26Δsfp as compared to wheat primed by A26 wild type (Control). This sfp gene activation, in fact, resulted in about the same dry weight and survival improving characteristics as AZP2.

Furthermore, FIGS. 9A and 9B show that slightly improved soil nutrition dramatically enhanced the beneficial effects of AZP2 priming on wheat biomass and survival during drought stress (compare AZP2 in FIGS. 9A and 9B with Drought AZP2 in FIGS. 1 and 4). Thus, whereas about 60% of the AZP2-primed wheat seedlings survived at day 7 in sand (FIG. 4) 80% of AZP2-primed wheat seedlings survived in sand with greenhouse soil after 14 days (FIG. 9B).

AZP2 improved plant dry weight 100% and AF about 300% under salt stress exposure (FIG. 9A). AZP2 primed plant survival was 2 times higher and AF primed plant survival was 4 times than control plants after 14 days of salt stress exposure (FIG. 9B). FIGS. 9A and 9B confirm AZP2 ability to induce stress tolerance and improve growth under two osmotic stresses (drought and salt stress) indication that the bacteria can also tolerate other osmotic stresses such as e.g. heavy pollutants.

Comparison of AZP2, AZP2/A26 and AZP2/AF Priming on Winter Wheat and Barley.

The seeds of spring wheat (*Triticum aestivum* L. cv. Stava, and Olivin) and barley (*Hordeum vulgare* L.cv. Barbo and Beatrix) were used to assess drought stress tolerance enhancing effect of the *B. thuringiensis* strain AZP2 and its combinations with *P. polymyxa* A26 and *A. faecalis* AF. Results were similar for both wheat and barley and results for wheat cv Stava are shown in Table 3.

The seeds were surface sterilized with 5% chlorine solution. The bacteria were grown in Tryptone Soy Broth (TSB) medium at 28° C. overnight. Culture density was determined by colony forming unit analysis (CFU). Priming was performed by soaking grains in solutions containing $10^7$ bacteria $ml^{-1}$ for 4 hours at 28° C. For the control treatment, another set of grains was soaked in sterile TSB media. A26 and AF were grown overnight in Luria Broth (LB) or TSB, pelleted and washed in 0.9% saline (NaCl). Grains were planted in sand soil and left to grow in controlled environment in a MLR-351H (Phanasonic, Ill., USA) growth chamber with 24/16° C. (day/night) temperature, and 16 h photoperiods at 250 μmol $m^{-2}$ $s^{-1}$ and 60% humidity for three to seven days. After the period seedlings were watered with *P. polymyxa* A26 ($10^6$ cells per ml) or *A. faecalis* (AF) solution ($10^6$ cells per ml). Control plants were treated with 0.9% saline. For drought stress treatment, 20-days-old plants were left to grow without water for 10 days (FIGS. 9A and 9B.).

Figure 10:
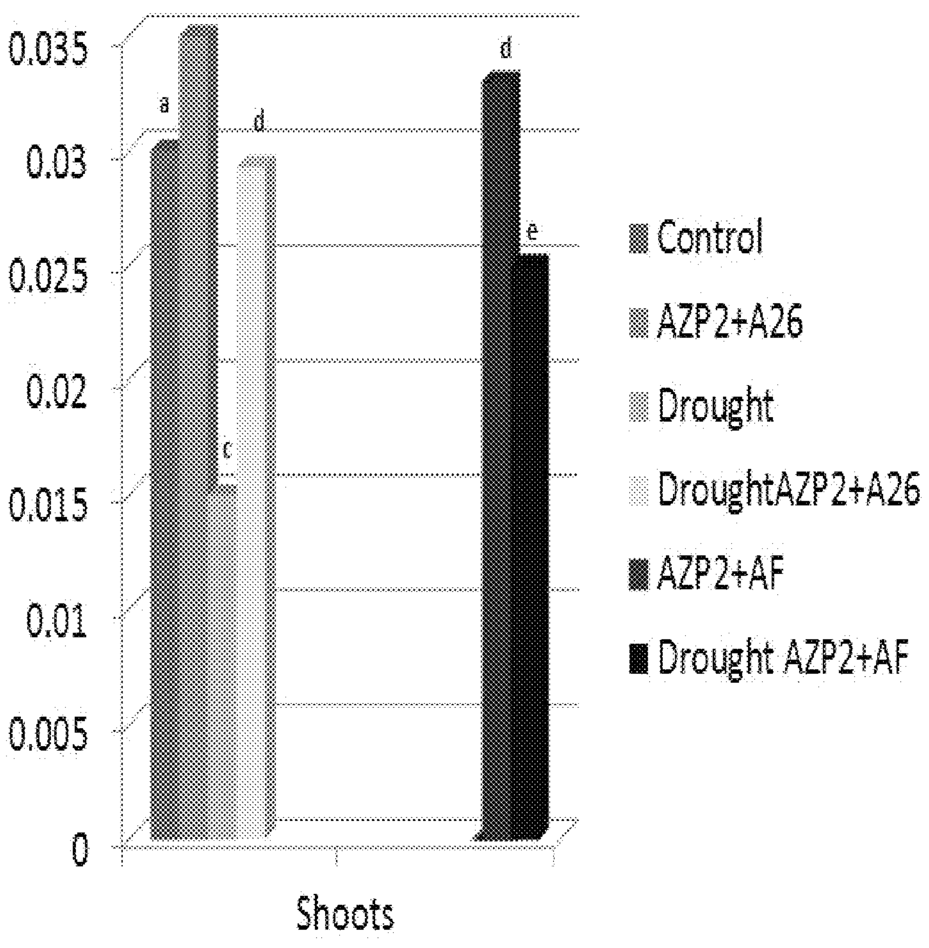
FIG. 10 illustrates the comparative effect of AZP2/A26 and AZP2/AF combinations on dry weight on winter wheat shoots (cv Stava and Olivin) grown in sand with normal watering (unstressed) and exposed to drought stress.
Figure 11:
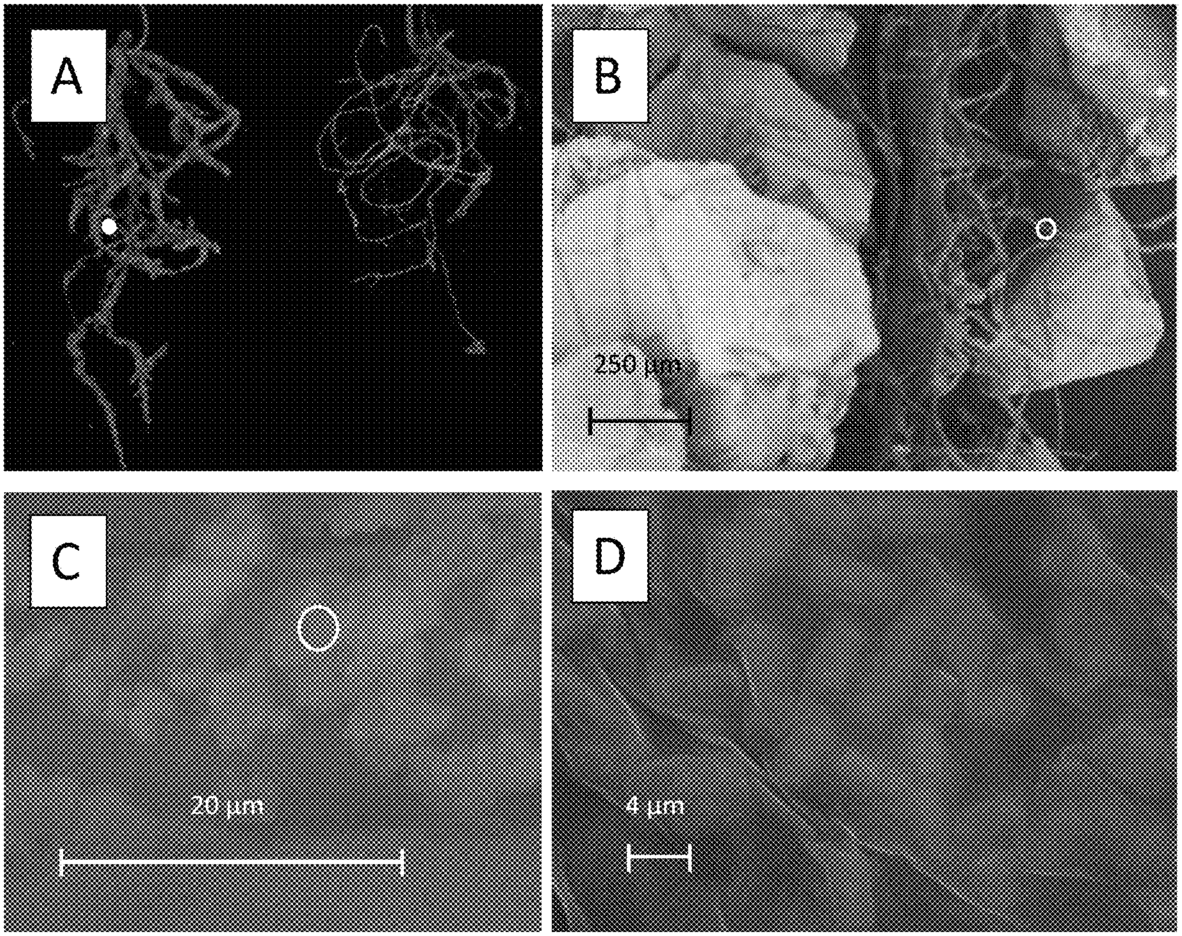
FIG. 11 illustrates sand soil mulch (A, B) and biofilm formation (C, D) on winter wheat (cv. Stava) root hairs. SEM micrographs of the samples were obtained with an environmental Hitachi TM-1000-μDex variable pressure scanning electron microscope equipped with EDAX analysis. Samples were deposited on a carbon tape and coated by gold using Cressington Sputter Coater 108 auto

FIGS. 10 and 11, Table 2 and Table 3 illustrate that AZP2 priming followed by A26 and AF priming improved AZP2 plant growth promoting effect. Wheat and barley dry weight improved 20% in combination with A26 and 10% in combination with AF grown in nutritionally poor soil with normal watering (Table 2). There are many traits that facilitate plant survival and growth under drought and nutrition deprivation stress, e.g. capacity of root to extract moisture and nutritional elements from soil. This can be achieved by various ways. In one of our examples, AF induces longer roots (Table 3). Our results show that root hair length and density may have major importance as stress tolerance enhancement strategy under the conditions tested. Combination of AZP2 and A26 priming resulted in 4.5 and 2.5 times root hair length and density improvement. Table 2 illustrates that the bacterial combination resulted in highest dry weight (100%) and survival increase (575%). AZP2 combination with AF increased plant dry weight 85% and survival 550%. The detailed analysis of plat root systems reveals that plant lateral root length and total root length both were improved about 150% by AZP2 and AF combination. Root hair length and density improvement was about 2.5 and 1.5 times respectively, which is significantly less than AZP2+A26 combination (Table 3).

Another important root trait is self creation of soil mulch-biofilm. Root hair forms a good matrix for the bacterially excreted biofilm. As a measure of biofilm we show soil attached to the sticky bacterial biofilm on plant root (Table 3 and FIG. 11). Bacterial biofilms are comprised of cells and extracellular matrix and can produce the layer around root hair (FIG. 11). The dense biofilm matrix limits diffusion of biologically active compounds and elements secreted by bacteria and these are therefore concentrated for plant uptake. It also substantially improves root soil contact and enhances significantly plant nutrient or biologically active compound acquisition from soil or bacterial origin (Table 3). As a result of this plant nutrient content (P/K/N/Ca/) is increased.

Another important trait under successful establishment is root maturity regulation. After the stress exposure the untreated plant root system was formed of dry thin roots with very few fresh vital roots. Significantly higher number of fresh roots was induced by AZP2 which further increased in combination with A26 and AF. This confirms the biofilm soil mulch protective rote but also indicates that certain regulatory signaling compounds are produced in the bacterial biofilm which regulate the root maturity. The priming of wheat and barley cultivars with above mentioned bacterial combinations reveal synergistic effects of the bacterial isolates. Plant seedling successful establishment is required for its survival. Hence high germination rate is of prime importance. Table 3 illustrates that 100% of AZP2 primed seeds germinated under normal and stress condition. Further, depending on what stress the plant is exposed to, other bacteria can be added. The best dry weight and survival under drought stress is achieved by AZP2+A26 combination. A26 adds density and length of root hair as well as rich slimy biofilm production. A26Δsfp produces even slimier biofilm on the root hair. AF induced root length. AZP2+AF ability for root hair induction better than AZP2 alone yet significantly lower than AZP2+A26 combined activity. Yet AZP2+AF combination resulted in longer roots than AZP2+A26 combination. AZP2+AF dry weight and survival enhancement is higher than in case of AZP2 yet lower than AZP2+A26 combination. In case there is a risk of certain pathogens A26 or AF can be selectively chosen.

Hence the above described bacterial combination gives good grounds for sustainable precision agriculture with relatively low costs. The farmer is aware of the conditions of his field and the particular crop plants he wants to sow. In case only germination rate and some root hair growth and density improvement would be sufficient then AZP2 treatment alone should be performed. This will ensure the seedling strengthening under moderate nutritional and drought stress conditions. In the situation of severe abiotic stress longer roots and higher root hair density would be beneficial. This will be performed by A26 or AF inoculation. In case of pathogen risk the farmer will choose between AF and A26 dependent on their specificity for pathogen antagonism.

TABLE 3

Comparison of AZP2 AZP2/A26 and AZP2/AF priming on winter wheat

| | Control | AZP2 | AZP2 + A26 | AZP2 + AF | Drought |
|---|---|---|---|---|---|
| Plant survival improvement (%) | 100 | 100 | 100 | 100 | |
| Plant dry weight increase (%) | | 9 | 20 | 10 | |
| Germination rate[1] (%) | 72 | 100 | 100 | 100 | 50 |
| Lateral root count[2] | 266 ± 76.36$^{ab}$ | 235 ± 21.21$^{ab}$ | 240 ± 19$^{ab}$ | 250 ± 20$^{ab}$ | 181 ± 15.55$^{c}$ |
| Total lateral root length (cm) | 263.11 ± 11.46$^{a}$ | 182.5 ± 23.33$^{b}$ | 176 ± 4.94$^{b}$ | 250 ± 4.37$^{a}$ | 89 ± 11.31$^{d}$ |
| Longest root length (cm) | 28.38 ± 1.41$^{ab}$ | 27.55 ± 2.19$^{ab}$ | 18 ± 2.12$^{b}$ | 25 ± 4.1$^{ab}$ | 20.69 ± 1.22$^{c}$ |
| Total root lengths (cm) | 352.6 ± 10.45$^{a}$ | 232.5 ± 9.19$^{ab}$ | 208 ± 17.67$^{b}$ | 350 ± 19.8$^{a}$ | 116.13 ± 19.61$^{c}$ |
| Soil attached to root[3] (g/g dry root) | 62.02 ± 18.93$^{a}$ | 91.60 ± 29.5$^{ab}$ | 115 ± 21$^{b}$ | 105 ± 20.7$^{b}$ | 10 ± 5.02$^{c}$ |
| Root hair length[4] (mm) | 0.74 ± 0.2$^{a}$ | 1.5 ± 0.5$^{b}$ | 4.1 ± 0.4$^{b}$ | 3 ± 0.2$^{b}$ | 0.84 ± 0.2$^{a}$ |
| Root hair density (number per $mm^3$) | 24 ± 3$^{a}$ | 30 ± 2$^{ab}$ | 60 ± 4$^{c}$ | 40 ± 2$^{b}$ | 24 ± 2 a |
| Number of fresh roots per plant | | | | | 3 ± 1 |
| Water use efficiency[5] (g per g plant) | 0.10533 ± 0.003$^{d}$ | 0.10867 ± 0.002$^{d}$ | 0.10777 ± 0.002$^{d}$ | 0.1082 ± 0.02$^{d}$ | 0.08016 ± 0.003$^{b}$ |
| P/K/N/Ca content in shoots[6] (g per kg) | Nt | Nt | Nt | Nt | 1.5/25/11/2.4 |
| Maximal PS II efficiency (Fv/Fm)[7] | Nt | Nt | Nt | Nt | 0.6 |

| | AZP2 Drought | AZP2 + A26 Drought | AZP2 + AF Drought |
|---|---|---|---|
| Plant survival improvement (%) | 500 | 570 | 540 |
| Plant dry weight increase (%) | 78 | 100 | 85 |
| Germination rate[1] (%) | 100 | 100 | 100 |
| Lateral root count[2] | 192.5 ± 3.53$^{bc}$ | 180 ± 14.14$^{c}$ | 230 ± 14.14$^{ab}$ |
| Total lateral root length (cm) | 142.14 ± 31.31$^{bc}$ | 110.43 ± 6.03$^{c}$ | 249.53 ± 11.3$^{a}$ |
| Longest root length (cm) | 23.16 ± 1.18$^{bc}$ | 18 ± 1.76$^{b}$ | 26 ± 1.76$^{ab}$ |
| Total root lengths (cm) | 226.15 ± 10.11$^{ab}$ | 150 ± 6.01$^{b}$ | 300 ± 6.01$^{a}$ |
| Soil attached to root[3] (g/g dry root) | 25.29 ± 10.84$^{bc}$ | 36.57 ± 3.15$^{d}$ | 31.57 ± 3.1$^{f}$ |
| Root hair length[4] (mm) | 1.9 ± 0.2$^{b}$ | 4.2 ± 0.4$^{c}$ | 2.5 ± 0.2$^{bc}$ |
| Root hair density (number per $mm^3$) | 30 ± 1$^{ab}$ | 62 ± 4$^{c}$ | 39 ± 2$^{b}$ |
| Number of fresh roots per plant | 10 ± 2 | 15 ± 1 | 13 ± 1 |

TABLE 3-continued

Comparison of AZP2 AZP2/A26 and AZP2/AF priming on winter wheat

| | | | |
|---|---|---|---|
| Water use efficiency[5] (g per g plant) | 0.13484 ± 0.012[c] | 0.17489 ± 0.011[b] | 0.15489 ± 0.012[c] |
| P/K/N/Ca content in shoots[6] (g per kg) | 1.8/2814/2.8 | 2.3/35/18/3.6 | 2.2/32/18/3.5 |
| Maximal PS II efficiency (Fv/Fm)[7] | 0.8 | 0.8 | 0.8 |

[1]Results for wheat *Triticum dicoccoides* (cv. Stava) are shown in the Table.

[2]Plant root counts and lengths were performed visually and using Root Reader3D Imaging and Analysis [7].

[3]Twelve plantlets per treatment were sampled. Roots with adhering soil (RAS) were carefully separated from bulk soil by shaking. Soil and root dry mass (RT) was recorded after drying the samples at 105° C., and RAS/RT ratio was calculated.

[4]Twelve plantlets were carefully separated from soil by shaking. Flowingly plantlets roots were washed in distilled water and left to dry in Petri dishes containing 5 ml of water. Dried root system was evaluated using Zeiss LSM 710 microscope

[5]Water use efficiency = Total dry mass/Total water usage

[6]SS ISO 13878 and SS 028126-3 methods were used for analysis.

[7]Three leafs of identical size from 10 seedlings were used for chlorophyll fluorescence measurements with a PAM fluorometer (Imaging PAM, Walz, Effeltrich, Germany) based on Nagy et al. (2004) [8]. Dark-adapted seedlings (15 min darkness before the measurement) were used for the measurement of maximal photosystem II (PSII) efficiency (FvIFm) with a white Maximal PS II efficiency (Fv/Fm) saturating pulse (3000 pE $m^2$ $S^{-1}$) of 0.7 s duration.

Inhibitory Effect of AZP2, A26 and AF to Fungal Pathogens

The rhizobacterial strains of the embodiments were also tested with regard to antagonism against various agricultural pathogens of various plants. The pathogens tests for in this experiment are all of economic importance throughout Europe.

Two-week-old plantlets grown in MS medium were sequentially preinoculated with AZP2 and A26 or with AZP2 and AF. AZP2, A26 and AF were grown overnight in Luria Broth (LB) or Tryptic Soya Broth (TSB), pelleted and washed in 0.9% saline (NaCl) Plant seeds were soaked for 4 h in *B. thuringiensis AZP*2 0.9% saline ($10^6$ cells per ml) and left to germinate in soil for three to seven days. After the period seedlings were watered with *P. polymyxa* A26 ($10^6$ cells per ml) or *A. faecalis* (AF) solution ($10^6$ cells per ml). Control plants were treated with 0.9% saline.

Another method of inoculation with bacterial spore suspensions can be used. Two week old plant seedlings are grown in greenhouse soil and watered with spore solutions of AZP2 and A26 or AZP2 and AF sequentially. Spore solution medium is prepared as follows:

| | |
|---|---|
| Bacto nutrient broth (Difco) | 8 g per liter |
| 10% (w/v) KCl | 10 ml |
| 1.2% (w/v) $MgSO_4$•$7H_2O$ | 10 ml |
| 1M NaOH | ~1.5 ml (pH to 7.6) |

The volume was adjusted to 1 liter with $ddH_20$ and pH to 7.6, and autoclaved and allowed to cool to 50° C. Just prior to use, the following sterile solutions were added:

| | |
|---|---|
| 1M $Ca(NO_3)_2$ | 1 ml |
| 0.01M $MnCl_2$ | 1 ml |
| 1 mM $FeSO_4$ | 1 ml |

TABLE 4 fungal pathogen inhibitory effect of AZP2, AZP2/A26 and AZP27AF

| Plant | Pathogen | AZP2 | AZP2 + A26 | AZP2 + AF |
|---|---|---|---|---|
| | | Seedling survival (%) | | |
| Alfa alfa | *Phythophthora megasperma* | 83 | | |
| Tobacco | *Phythophthora nicotianae* | 80 | | |

TABLE 4-continued fungal pathogen inhibitory effect of AZP2, AZP2/A26 and AZP27AF

| Plant | Pathogen | AZP2 | AZP2 + A26 | AZP2 + AF |
|---|---|---|---|---|
| | | Seedling survival (%) | | |
| Cucumber | *Pythium aphanidermatum* | 75 | | |
| Peanut | *Sclerotinia minor* | 76 | | |
| Tomato | *Pythium torulosum* | 80 | | |
| *A. thaliana* | *Pythium aphanidermatum* | | 87 | |
| | *Phythophthora palmivora* | | 100 | |
| | *Aspergillus niger* | | 90 | 100 |
| | *Fusarium oxysporum* | | 90 | 100 |
| Wheat | *Bortrytis cinerea* | | 85 | 100 |
| | *Microdochium nivale* | | 80 | |
| | *Fusarium graminearum* | 86 | | |
| | *Oculimacula yallundae* | | 75 | |
| | | 83 | | |
| Wheat/barley | *Fusarium culmorum* | | 75 | |
| | *Fusarium graminearum* | | 75 | |

Table 4 above illustrates the inhibitory effect of AZP2 and the combination of AZP2+A26 AZP2+AF to various fungal pathogens by significantly improving the number of surviving plants.

AZP2/A26 Induced Inhibition of DON and ZEA Production

Wheat and barley *Fusarium* head blight (FHB) caused by *F. graminearum* and *F. culmorum* is a disease of particular importance. Infection of grain seedlings leads to loss of grain yield and quality of grain size, weight, germination rate, protein content, baking quality of flour and other technological parameters. The most serious consequence of FHB is the contamination of grain with mycotoxins. The trichothecenes, particularly deoxynivalenol (DON) and zearalenone (ZEA) and their acetylated derivatives, are the most frequently encountered mycotoxins in FHB in Europe.

The effect of AZP2 and A26 on the production of DON produced by *F. graminearum* and *F. culmorum* was investigated.

Wheat seeds (20 g) were dipped in 100 ml flask with 10 ml of water and autoclaved at 121° C. for 30 min. and treated with $10^7$ spore suspensions of AZP2/A26. Spores were prepared in Difco Sporulation Medium:

| | |
|---|---|
| Bacto nutrient broth (Difco) | 8 g |
| 10% (w/v) KCl | 10 ml |

-continued

| | |
|---|---|
| 1.2% (w/v) $MgSO_4 \cdot 7H_2O$ | 10 ml |
| 1M NaOH | ~1.5 ml (pH to 7.6) |

The volume was adjusted to 1 liter with $ddH_20$ and autoclaved. Just prior to use, the following sterile solutions were added:

| | |
|---|---|
| 1M $Ca(NO_3)_2$ | 1 ml |
| 0.01M $MnC_{l2}$ | 1 ml |
| 1 mM $FeSO_4$ | 1 ml |

Conidial suspensions of pathogens of two week old potato dextrose agar (PDA) plates were inoculated to flasks. Extraction and quantification of DON and ZEA was performed using liquid chromatography—mass spectrometry (LC-MS). In Table 5, values with the same letters indicate those that are not statistically different (P≤0.05 by ANOVA).

TABLE 5

AZP2/A26-induced inhibition of DON and ZEA production

| | After 7 days | | After 14 days | |
|---|---|---|---|---|
| Mycotoxin (mg per kg) | DON | ZEA | DON | ZEA |
| *F. culmorum* | $25.5^a$ | $40^a$ | $80.2^a$ | $70^a$ |
| *F. culmorum* w. AZP2/A26 | $5.6^b$ | $0.02^b$ | $6.7^b$ | $0.05^b$ |
| *F. graminearum* | $5.3^a$ | $10^a$ | $6.8^a$ | $40^a$ |
| *F. graminearum* w. AZP2/A26 | $2.7^a$ | $0.04^b$ | $2.8^b$ | $O.06^b$ |

The results presented in Table 5 clearly indicate that the strains AZP2 and A26 of the embodiments are able to significantly reduce the amount of DON and ZEA produced by fungal pathogens in AZP2/A26-treated plants.

Enhancement of Phosphorus, Nitrogen and Calcium Content in Plant Shoots

Phosphorous, nitrogen and calcium are major essential macronutrients for biological growth and development. The ability of some microorganisms to convert insoluble phosphorus (P) to an accessible form, like orthophosphate, is an important trait in a bacterium for increasing plant yields. It is generally known that bacterial ability to lower the pH is responsible to P release.

AZP2 is significantly enhancing P, N and Ca content in plant wheat and barley leaves. This is further improved in combination with A26 and AF. This is be obtained by the bacterial induction of root hair length and density and biofilm formation on the root hair. Root hair can substantially increase root soil contact. Hence cause significant increase in plant nutrient uptake. Bacterial biofilms are comprised of cells and extracellular matrix and can produce the sticky layer around root hair (FIG. 11). The dense biofilm matrix limits diffusion of biologically active compounds and elements secreted by bacteria and these are therefore concentrated for plant uptake.

The effect of AZP2, A26 and A26Δsfp in solubilizing insoluble inorganic phosphorus in soil and making it available to plants was investigated. This ability was investigated by the change of pH (from pH 7.3 in broth cultures) by a pH meter during 36 hours of incubation.

AZP2, A26 and A26Δsfp were able to lower the pH to 6.

Soil Restoration

The rhizobacterial strain AZP2, due to its biofilm formation ability, can improve soil texture by reducing soil bulk density and enhancing soil porosity. The ability is further facilitated in combination with the A26 strain and A26Δsfp strain. Soil bulk density ranged from 0.9 to 1 g/$cm^3$ for AZP2 and A26 treated soil versus control treatment where the bulk density was about 1.4 g/$cm^3$. This may have a significant impact on how vegetation communities establish and develop in nutritionally poor soil. Bulk density values higher than about 1.4 g/$cm^3$ indicate possible limitations to root growth and penetration, typical bulk densities for cultivated soils are 1.0 to 1.25 g/$cm^3$.

Flocculation Ability

It is further stated that AZP2, A26 and A26Δsfp exhibit flocculation ability Flocculants are compounds used to precipitate insoluble substances. The purpose of coagulation and flocculation is to cause small pollutant particles such as metals to aggregate and form large enough floc so that they can be separated from the wastewater through sedimentation. Organic polymers isolated from microbial biofilms are added to wastewater and then flocculation tanks mix the water to promote flocs and subsequent physical separation.

The microbial flocculants produced in AZP2, A26 and A26Δsfp supernatant were applied to 10 mL 4% kaolin clay suspension, mixed with 0.2 ml 1% $CaCl_2$) solution (pH 7.0) and the absorbance OD550 of the suspension was measured by spectrophotometer after 10 min settlement. Flocculation rate N was calculated according to the formula:

$$N = \frac{A - A0}{A0} \times 100$$

wherein A0 is the OD550 obtained in control test, and A is the OD550 measured in the tube with the bacterial supernatant. Flocculation rate of A26Δsfp supernatant was 88.9%, 80% and 75% of A26 and AZP2, respectively.

Bacterial Isolation of *Paenibacillus polymyxa* B

*Paenibacillus polymyxa* B was isolated from salty rice rhizosphere at Giza, Egypt, Tina plain N 31° 00.2640 E 32° 39.9640 at an elevation of 13 m.

The isolation and identification protocols were as disclosed in [1]. Briefly, the plant roots were carefully shaken and washed in sterile distilled water to remove all loosely attached soil and rock powder and to collect bacteria intimately linked to the plant root. Plants were placed in sterile plastic bags, transferred to the laboratory, and then stored at +4° C. until they were processed in the next day.

Plant rhizosphere material (1 g) was homogenized as described by the manufacturer using FastPrep Instrument (BIO 101® Systems). Hence, the rhizosphere macerate contains bacteria in the endorhizophere.

Plant rhizosphere material was suspended in sterile PBS (137 mM NaCl, 2.7 mM KCl, 10 mM sodium phosphate dibasic, 2 mM potassium phosphate monobasic, pH of 7.4).

The content of endospore-forming bacteria was determined after heat treatment of the soil or plant material suspension at 80° C. for 30 min. Tryptic Soy Agar (TSA) plates were inoculated with 100 μL of these suspensions, corresponding to $10^{-3}$~$10^{-5}$ g soil or plant rhizosphere material per plate. All agar media contained 15 g agar and 50 mg cycloheximide, to reduce fungal growth, and had a pH of 7. The inoculated petri dishes were incubated for several weeks at room temperature (~21° C.), and at 30° C., 37° C., or 40° C. in boxes together with a beaker of water (to prevent drying of the agar).

The colonies for the endospore forming bacteria were studied for plant drought stress tolerance enhancement and sequenced from that plate.

VOCs Sampling and Analysis

Volatiles were trapped by sampling 4 L of the air from the Walz GFS-3000 cuvette outlet into a multibed stainless steel cartridge, and analyzed by GC-MS as in [4, 5]. Ethylene emission rate was measured at days 0, 2, 5, 8 and 10 days after stress application using Picarro G1106 real-time ethylene analyzer (Picarro, Inc, CA, USA). The ethylene analyzer was linked to GFS-3000 gas-exchange system through a bypass loop.

Data Confirmation and Validation

Experiments were repeated three times to confirm reproducible plants phenotypes. Replicated data were analyzed by three-way ANOVA (stress×strain×stress exposure time), and all treatment effects were considered significant at $P \leq 0.01$.

Results

Figure 12A:
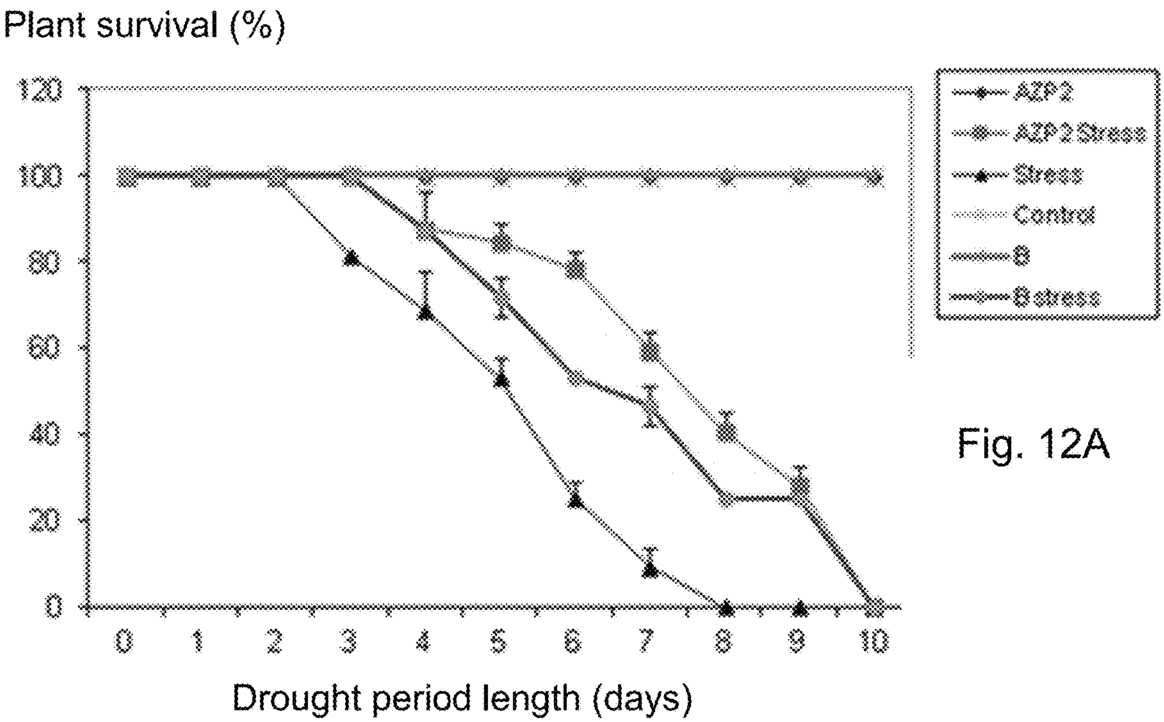
FIG. 12A illustrates the effect of *B. thuringiensis* AZP2 and *P. polymyxa* B priming on plant survival grown with water (control, AZP2 and B) or without water (stress, AZP2 stress and B stress) for 10 days.

Ten-days-old wheat plants were exposed to severe drought stress of 10 days without watering. During the first two days of stress exposure, no visible signs of drought were recorded. However, after the third day, plant survivorship decreased significantly, and this trend became emphasized with increasing the stress period. Less than 20% of the un-primed plants could survive for 7 days of stress, and none could survive for eight days of drought (FIG. 12A). In contrast, *Bacillus thuringiensis* AZP2 primed plants exhibited a delayed initial response to drought stress. After four days of stress exposure, 100% of AZP2 primed plants survived. Furthermore, more than 60% of the *B. thuringiensis* AZP2 primed plants were able to cope with drought stress for 7 days, and about 20% of *B. thuringiensis* AZP2 primed plants were able to survive even after nine days of stress (FIG. 12A). The positive effects seen with AZP2 were better than the corresponding effects seen with *P. polymyxa* B.

Figure 12B:
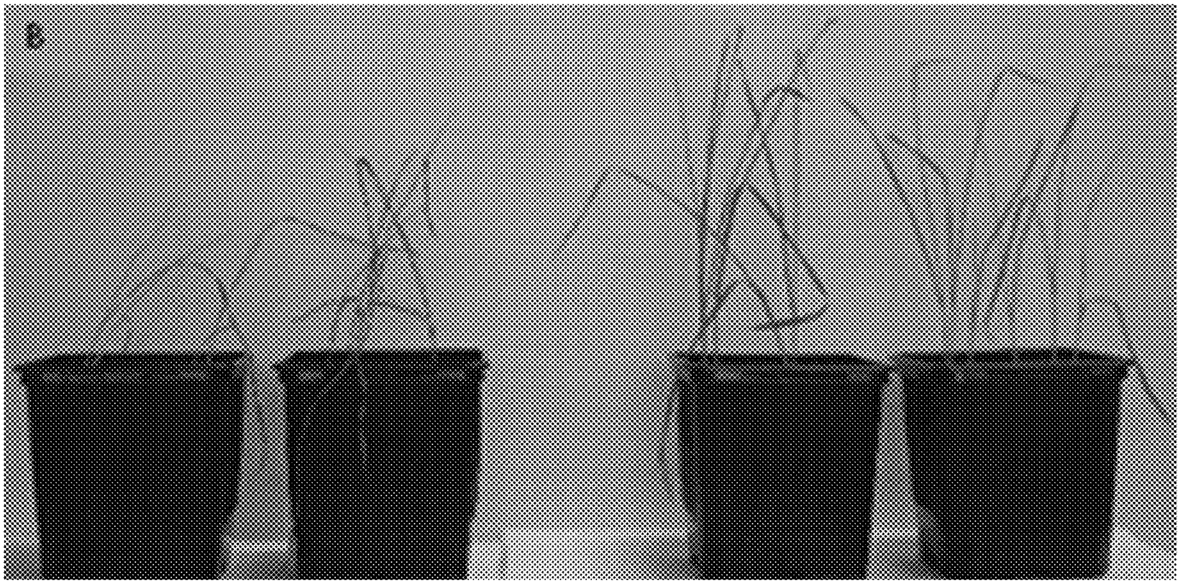
FIG. 12B illustrates wheat seedlings phenotype after 8 days drought stress; *B. thuringiensis* AZP2 primed stressed plants (right) are compared to stressed plants without inoculation (left).

Eight days of stress exposure resulted in a major phenotypic differences (FIG. 7B). The un-primed plants were severely damaged after such acute water stress. On the other hand, *B. thuringiensis* AZP2 priming strongly assisted in avoiding and reducing the drought-induced damage (FIG. 12B). All key whole plant characteristics, root fresh and dry weight and water contents were significantly higher in case of AZP2 priming (FIG. 1). In comparison to other isolates, the AZP2 grown on rock under drought heat and UV stress exhibited the best potential to enhance plant drought stress tolerance, see Table 6 below.

TABLE 6

Effect of bacterial priming on drought stressed *Arabidopsis thaliana* survival

| Bacterial strain | Origin | Plant survival %* |
|---|---|---|
| Control | — | 0 |
| *Bacillus thuringiensis* AZP2 | Mt. Lemmon, AZ, USA | 43 ± 3 |
| *Paenibacillus polymyxa* B | Tina plain, Egypt | 22 ± 3 |
| *P. polymyxa* A26 | SFS, EC, Israel | 16 ± 3 |
| *B. cereus* A4 | SFS, EC, Israel | 15 ± 3 |
| *B. megaterium* A2 | SFS, EC, Israel | 15 ± 3 |
| *B. pumilus* A1 | SFS, EC, Israel | 10 ± 3 |
| *P. polymyxa* E1 | NFS, EC, Israel | 0 |
| *B. cereus* E1 | NFS, EC, Israel | 0 |

TABLE 6-continued

Effect of bacterial priming on drought stressed *Arabidopsis thaliana* survival

| Bacterial strain | Origin | Plant survival %* |
|---|---|---|
| *B. megaterium* E2 | NFS, EC, Israel | 0 |
| *B. pumilus* E3 | NFS, EC, Israel | 0 |

*Plant survival grown without water for eight days is shown.
SFS, EC—South Facing Slope, 'Evolution Canyon'
NFS, EC—North Facing Slope, 'Evolution Canyon'

Figure 14A:
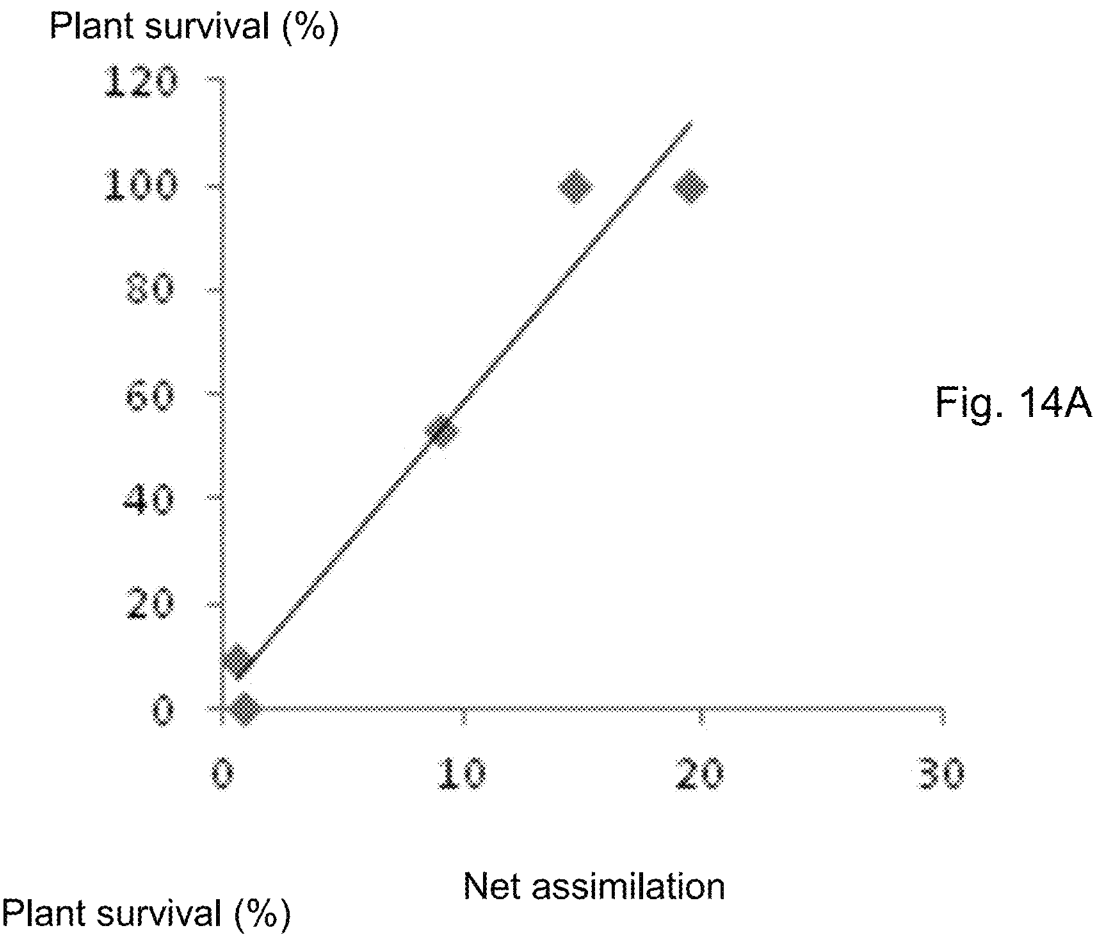
FIGS. 14A and 14B illustrate correlation analysis between plant survival and some photosynthetic parameters (FIG. 14A: net assimilation and FIG. 14B: stomatal conductance) of drought stressed (0, 2, 5, 8 and 10 days without water) wheat seedlings.
Figure 14B:
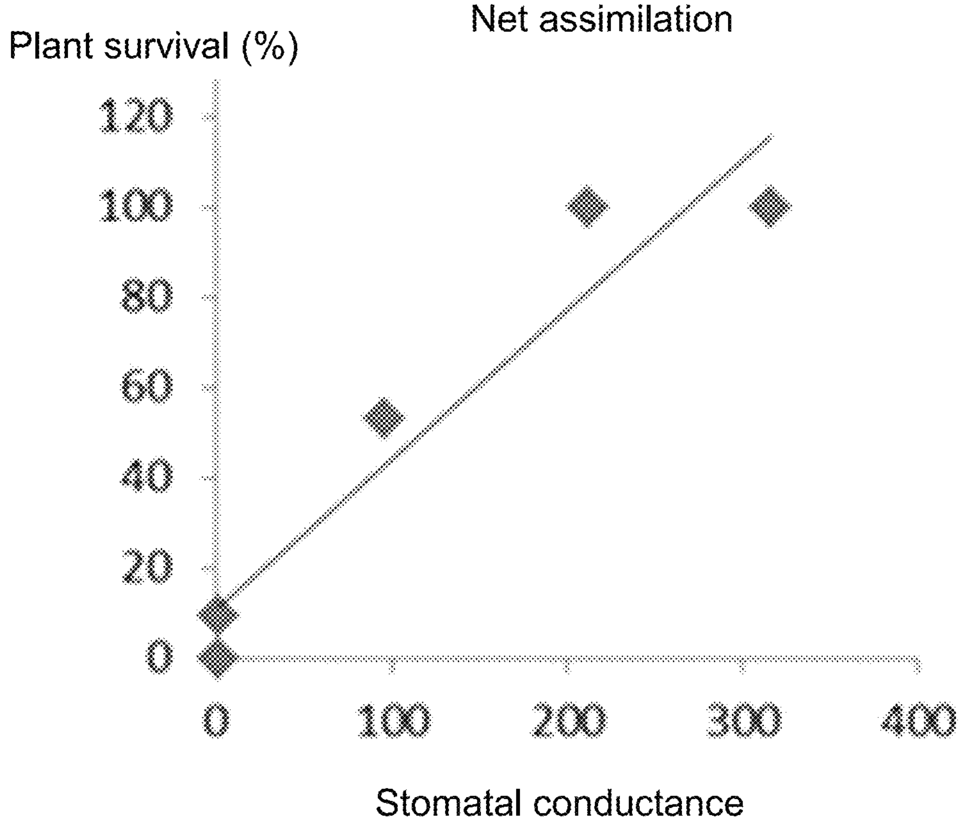

In document [2] the very first rhizobacterial plant drought stress tolerance enhancement was shown using the bacterium *Paenibacillus polymyxa* B strain. Therefore the pattern of *B. thuringiensis* AZP2 isolate in wheat drought stress tolerance enhancement was compared *P. polymyxa* B strain. Similar quantitative estimates, but slightly favoring AZP2 strain in survival rates, were recorded (FIG. 10A). Photosynthesis characteristics such as net assimilation rate, stomatal conductance and transpiration rate were monitored through the drought stress treatment in both primed and un-primed plants as well as in the controls. Under drought-stress, a steady decline in net assimilation rate was recorded in all stressed wheat plants (FIG. 7A). Net assimilation rate was almost totally inhibited in un-primed wheat plants after 8 days without water (FIG. 7A). However, *B. thuringiensis* AZP2 primed plants exhibited much higher net assimilation rate compared to the control, independently of whether the plants were stressed or not. The only exception was for 10 days drought-stressed primed plants where the net assimilation rate was almost completely inhibited. No significant difference in net assimilation rate among *B. thuringiensis* AZP2 and *P. polymyxa* primed plants was observed. A regression analysis demonstrated a very strong positive correlation between net assimilation rate and plant survivorship through the drought-stress period ($r^2=0.95$, $P<0.001$, FIG. 14A).

Stress- and priming-driven modifications in stomatal conductance (gs) and transpiration rate mirrored those in net assimilation rate. Un-primed control treatment showed relatively stable gs between 150 and 200 mmol $m^{-2}$ $s^{-1}$ throughout the course of the experiment (FIG. 7B). In contrast, stressed un-primed plants showed steady reduction in gs and transpiration rate during the drought treatment. *B. thuringiensis* AZP2 primed plants had significantly higher gs and transpiration rate (FIGS. 7A and 7B) whether drought-stressed or not. Stomatal conductance and transpiration rate were significantly higher for *B. thuringiensis* AZP2 than for *P. polymyxa* B primed plants (FIGS. 7A and 7B). Changes in stomatal conductance during the drought cycle were positively correlated with plant survivorship ($r^2=0.91$, $P<0.001$, FIG. 13B).

Figure 13A:
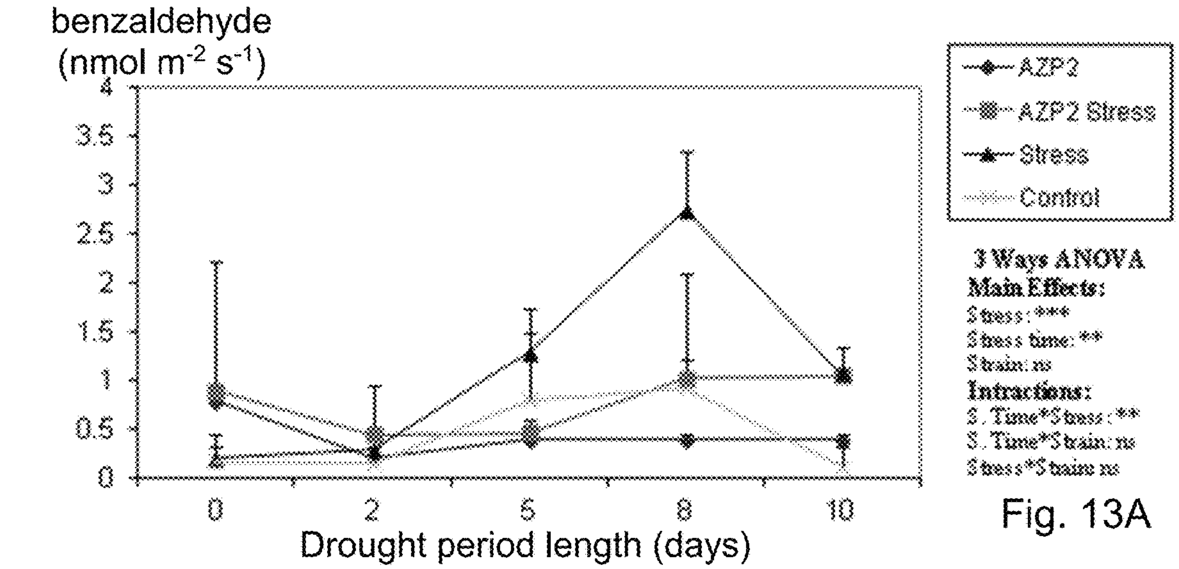
FIGS. 13A-13C illustrate benzaldehyde (FIG. 13A), β-pinene (FIG. 13B) and geranyl acetone (FIG. 13C) emission from leaves of drought stressed (0, 2, 5, 8 and 10 days without water) wheat after priming with *Bacillus thuringiensis* AZP2. Bars indicate standard errors between three biological replicates.
Figure 13B:
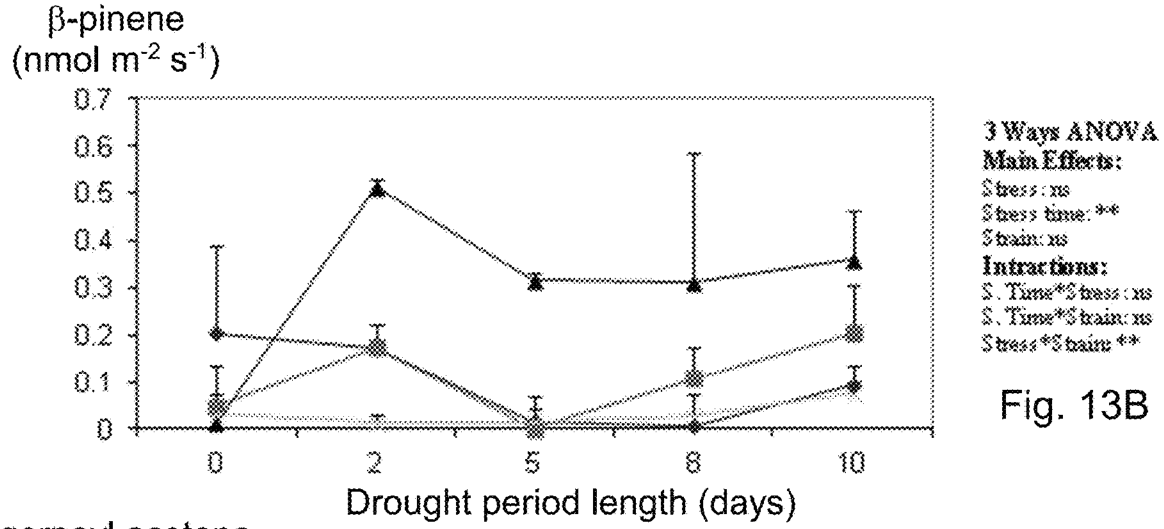

The GC-MS analysis showed that seven terpenoid and benzoid compounds were emitted from wheat leaves including α-pinene, limonene, p-cymene, α-phellandrene and camphene. However, only benzaldehyde, β-pinene and geranyl acetone showed a significantly distinctive pattern in response there plant drought stress tolerance was observed (FIGS. 13A and 13B). Benzaldehyde emissions increased with increasing the drought stress period; the emission reached its maximum levels when un-primed wheat plants were grown without water for 8 days (FIG. 13A). On the other hand, *B. thuringiensis* AZP2 primed stressed plants showed modest benzaldehyde emission compared to the un-primed stressed plants. Both *B. thuringiensis* AZP2 and

Figure 15A:
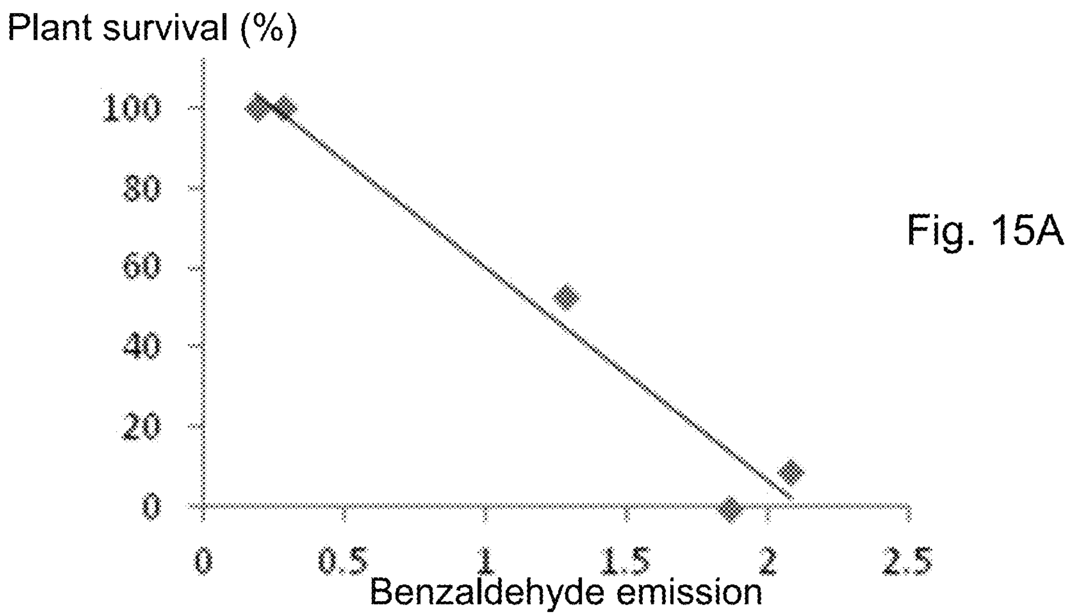
FIGS. 15A-15C illustrate correlation analysis between plant survival and benzaldehyde emission (FIG. 15A), plant survival and geranyl acetone emission (FIG. 15B) and net assimilation and geranyl acetone emission (FIG. 15C) of drought stressed (0, 2, 5, 8 and 10 days without water) wheat seedlings.

*P. polymyxa* B primed stressed plants showed relatively similar benzaldehyde emission pattern. However, increasing the drought stress periods more than 5 days resulted in a rapid benzaldehyde emission from *P. polymyxa* B primed stressed plants. Benzaldehyde emission was negatively correlated with plant survival % under stress conditions ($r^2$=0.96, FIG. 15A).

Low-level β-pinene emissions were detected from well-watered wheat plants independent of whether the plants were primed or not. However, two-fold higher β-pinene emissions were detected in 2 days drought-stressed plants, and the emissions further stabilized to somewhat lower steady levels for the rest of the study. *B. thuringiensis* AZP2 primed stressed plants did not show any significant difference in β-pinene emissions compared with the emission in the control treatment. However, four-fold higher β-pinene emissions were detected in *P. polymyxa* primed plants after 2 days drought stress, and these emissions subsequently decreased to the level recorded in the control treatment (FIG. 13B).

Figure 13C:
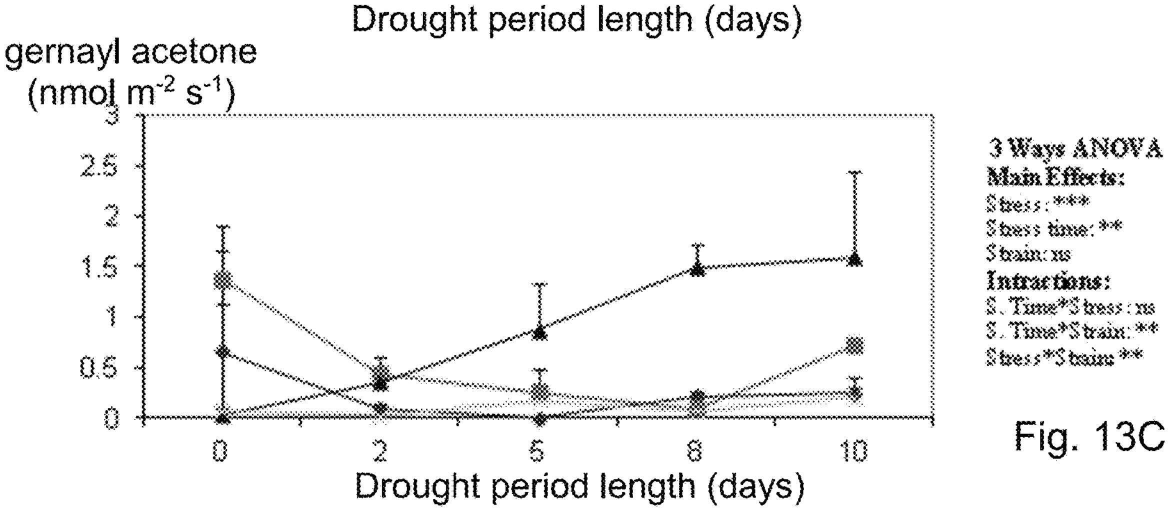
Figure 15B:
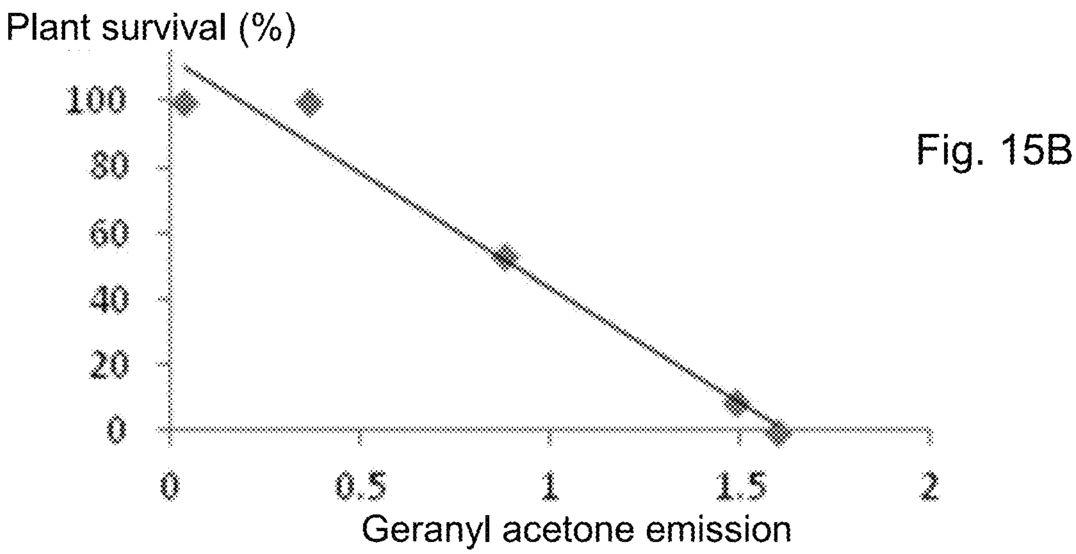
Figure 15C:
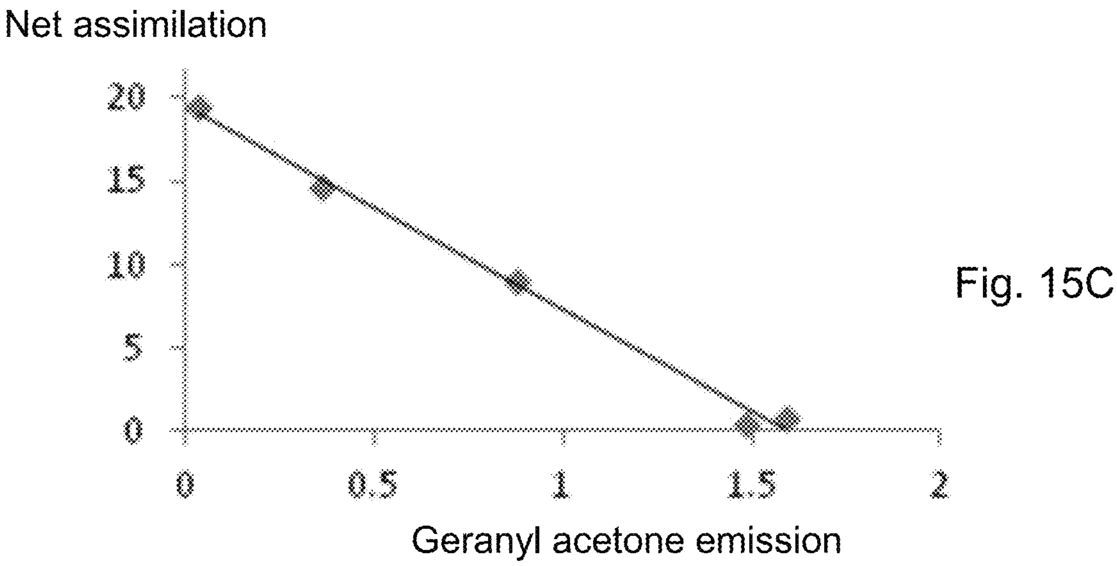

Drought stress induced a steady increase in the emissions of geranyl acetone (FIG. 13C). *B. thuringiensis* AZP2 primed stressed plants maintained a significantly lower geranyl acetone emission compared with their un-primed counterparts. The effect of priming with *P. polymyxa* B on geranyl acetone emission from stressed wheat plants was considerably higher compared to that recorded in *B. thuringiensis* AZP2 primed stressed plants. Strong negative correlations were observed between geranyl acetone emissions and plant survivorship ($r^2$=0.97, P<0.001, FIG. 15B) and net assimilation rate ($r^2$=0.994, P<0.001, FIG. 15C).

Different volatile organic compounds (VOC) are commonly emitted from plants leaves and these emissions are known to increase substantially under stress situations. Volatile emission causes a considerable amount of costly carbon losses and leads to physiological modifications connected with plant growth penalties. It is possible that some VOCs are just by products of various plant processes and others might be actively produced and used as sophisticated signals by plants to trigger stress tolerance. The results presented above clearly showed that the elevated emission of VOCs was always negatively correlated with plant growth and fitness under drought stress conditions. It has previously been demonstrated that plants may lose up to 10%, exceptionally more than 50%, of the carbon fixed by photosynthesis as cost for VOCs emission under stressful conditions. In addition to typical stress volatile hormones such as ethylene, stresses result in upregulation of several secondary metabolic pathways including terpenoid and shikimic acid pathway, and the observation of enhanced emission of certain terpenoids and benzoids in stress is in agreement with upregulation of these key secondary metabolic pathways.

Overall, the emission rates of induced VOCs are quantitatively associated with the severity of the stress. Thus, the observation that VOCs emissions were significantly reduced and were correlated with higher photosynthesis and plant survival under stress in primed plants suggests that the priming improved the stress tolerance. Reduced emissions of stress-induced VOCs further imply lower cost for VOC emission, potentially contributing to greater productivity under stress.

Several mechanisms have been suggested to explain the process of bacterial priming. Full genome sequencing of AZP2 confirmed the presence of several gene clusters which could be involved in observed drought tolerance enhancement and volatile emission. The results demonstrate that bacterial priming of drought stressed wheat plant resulted in significantly higher plant survival, photosynthesis and plant growth, and this was reflected in modifications in volatile profiles and total emission rates. The results collectively point out that bacterial priming could be the way to enhance plant stress tolerance. The results presented here provide encouraging evidence that use of plant root associated biofilm forming bacteria isolated from climatically stressful areas can importantly enhance crop productivity under water shortage and could be as a means of enhancing food security.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

[1] Timmusk et al., Bacterial distribution in the rhizosphere of wild barley under contrasting microclimates, PLoS ONE 6(3): e17968, pages 1-7, 2011

[2] Timmusk and Wagner, The plant-growth-promoting rhizobacterium *Paenibacillus polymyxa* induces changes in *Arabidopsis thaliana* gene expression: a possible connection between biotic and abiotic stress response, *Molecular Plant Microbe Interaction* 12(11), pages 951-959, 1999

[3] Copolovici and Niinemets, Flooding induced emissions of volatile signalling compounds in three tree species with differing waterlogging tolerance, *Plant, Cell and Environment* 33(9), pages 1582-1594, 2010

[4] Iriti and Faoro, Chemical diversity and defense metabolism: how plants cope with pathogens and ozone pollution, *International Journal of Molecular Science* 10(8), pages 3371-3399, 2009

[5] Copolovici et al., Emissions of green leaf volatiles and terpenoids from *Solanum lycopersicum* are quantitatively related to the severity of cold and heat shock treatments, *Journal of Plant Physiology* 169(7), pages 664-672, 2012

[6] Patil and Salunke, Bioflocculant exopolysaccharide production by *Azotobacter indicus* using flower extract of *Madhuca latifolia* L., *Applied Biochemistry and Biotechnology* 162(4), pages 1095-1108, 2010

[7] Clark et al., Three-dimensional root phenotyping with a novel imaging and software platform. *Plant Physiol* 156, pages 455-459 2011

[8] Nagy N E, et al., Effects of *Rhizoctonia* infection and drought on peroxidase and chitinase activity in Norway spruce (*Picea abies*). *Physiologia Plantarum* 120: pages 465-473, 2004

[9] U.S. Patent Application No. 2003/0228679 A1

[10] International Application No. WO 2009/091557 A1

[11] Marulanda et al., An indigenous drought-tolerant strain of *Glomus intraradices* associated with a native bacterium improves water transport and root development in *Retama sphaerocarpa, Microbial Exology* 52, pages 670-678, 2006

The invention claimed is:

1. A modified *Paenibacillus polymyxa* strain A26, A26ΔSfp, wherein the modified strain A26ΔSfp is *P. polymyxa* strain A26 deposited under deposition no. MSCL1306 genetically modified to be incapable of producing enzymatically active 4' phosphopantetheinyl transferase.

2. The modified strain A26ΔSfp according claim 1, wherein the modified strain A26ΔSfp is *Paenibacillus polymyxa* strain A26 deposited under depository no. MSCL1306 genetically modified by deletion of the complete nucleotide sequence of the gene encoding 4' phosphopantetheinyl transferase or at least a portion thereof.

3. A plant substrate comprising bacteria of the modified strain A26ΔSfp according to claim 1 or a bacterial composition comprising bacteria of the modified strain A26ΔSfp, and bacteria of at least one of *Bacillus thuringiensis* strain AZP2 deposited under depository no. MSCL1307 and *Alcaligenes faecalis* strain AF deposited under depository no. MSCL1394.

4. The plant substrate according to claim 3, wherein the plant substrate is selected from the group consisting of soil, peat, compost, vermiculite, perlite, sand, clay and mixtures thereof.

5. A method of improving tolerance of a plant against abiotic and/or biotic stress, the method comprising adding bacteria of the modified strain A26ΔSfp according to claim 1, or a bacterial composition comprising bacteria of the modified strain A26ΔSfp, and bacteria of at least one of *Bacillus thuringiensis* strain AZP2 deposited under depository no. MSCL1307 and *Alcaligenes faecalis* strain AF deposited under depository no. MSCL1394, to a plant substrate in which the plant is growing, in which the plant is to be planted, or which is used for the plant growth.

6. The method according to claim 5, wherein adding bacteria comprises adding the bacteria of the modified strain A26ΔSfp or the bacterial composition to the plant substrate in which the plant is growing, in which the plant is to be planted, or which is used for the plant growth to improve tolerance of the plant against abiotic stress.

7. The method according to claim 6, wherein the abiotic stress is osmotic stress.

8. The method according to claim 7, wherein the osmotic stress is selected from the group consisting of drought stress and salt stress.

9. The method according to claim 8, wherein the osmotic stress is drought stress.

10. The method according to claim 5, wherein adding bacteria comprises watering the plant substrate with an aqueous suspension of the modified strain A26ΔSfp or of the bacterial composition.

11. The method according to claim 5, wherein adding bacteria comprises adding spores of the bacteria of the modified strain A26ΔSfp to the plant substrate.

12. The modified strain A26ΔSfp according to claim 1, wherein the modified strain A26ΔSfp is *Paenibacillus polymyxa* strain A26 deposited under depository no. MSCL1306 genetically modified by replacement of the gene encoding 4' phosphopantetheinyl transferase with another nucleotide sequence.

13. The plant substrate according to claim 3, wherein the plant substrate is a plant growth medium.

14. The plant substrate according to claim 13, wherein the plant growth medium comprises water.

15. The method according to claim 5, wherein the plant substrate is a plant growth medium.

16. The plant substrate according to claim 15, wherein the plant growth medium comprises water.

17. The method to claim 5, wherein the plant substrate is selected from the group consisting of soil, peat, compost, vermiculite, perlite, sand, clay and a mixture thereof.

* * * * *

SEQUENCE LISTING

<160> NUMBER OF SEQ ID NOS: 6

<210> SEQ ID NO 1
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="unassigned DNA"
/note="PCR primer"
/organism="Artificial Sequence"

<400> SEQUENCE: 1
ctcatgcatc attgtaaatc actttcggac g 31

<210> SEQ ID NO 2
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
/note="PCR primer"
/organism="Artificial Sequence"

<400> SEQUENCE: 2
ctcggatcct cttaacagca catcggcat 29

<210> SEQ ID NO 3
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
/note="PCR primer"
/organism="Artificial Sequence"

<400> SEQUENCE: 3
ctctctagag aagtcttttt cattcgagct 30

<210> SEQ ID NO 4
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
/note="PCR primer"
/organism="Artificial Sequence"

<400> SEQUENCE: 4
ctcgggccct aatccgttca agcgtccat 29

<210> SEQ ID NO 5
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
/note="PCR primer"
/organism="Artificial Sequence"

<400> SEQUENCE: 5

-continued

```
agagtttgat cmtggctcag                                            20


<210> SEQ ID NO 6
<211> LENGTH: 891
<212> TYPE: DNA
<213> ORGANISM: Alcaligenes faecalis
<220> FEATURE:
<221> NAME/KEY: source
<222> LOCATION: 1..891
<223> OTHER INFORMATION: /mol_type="unassigned DNA"
      /note="16S rDNA"
      /organism="Alcaligenes faecalis"

<400> SEQUENCE: 6

gggcaatccg ggcagccttt aacatgcaag ttcgaacggc agcgcgagag agcttgctct     60

cttggcggcg agtggcggac gggtgagtaa tatatcggaa cgtgcccagt agcgggggat    120

aactactcga aagagtggct aataccgcat acgccctacg ggggaaaggg ggggatcgca    180

agacctctca ctattggagc ggccgatatc ggattagcta gttggtgggg taaaggctca    240

ccaaggcaac gatccgtagc tggtttgaga ggacgaccag ccacactggg actgagacac    300

ggcccagact cctacgggag gcagcagtgg ggaattttgg acaatggggg aaaccctgat    360

ccagccatcc cgcgtgtatg atgaaggcct tcgggttgta aagtactttt ggcagagaag    420

aaaaggtatc ccctaatacg ggatactgct gacggtatct gcagaataag caccggctaa    480

ctacgtgcca gcagccgcgg taatacgtag ggtgcaagcg ttaatcggaa ttactgggcg    540

taaagcgtgt gtaggcggtt cggaaagaaa gatgtgaaat cccagggctc aaccttggaa    600

ctgcattttt aactgccgag ctagagtatg tcagaggggg gtagaattcc acgtgtagca    660

gtgaaatgcg tagatatgtg gaggaatacc gatggcgaag gcagccccct gggataatac    720

tgacgctcag acacgaaagc gtggggagca aacaggatta gataccctgg tagtccacgc    780

cctaaacgat gtcaactagc tgttggggcc gttaggcctt agtagcgcag ctaacgcgtg    840

aagttgaccg cctggggagt acggtcgcaa gattaaactc aggaaatggc g            891
```